United States Patent
Nichols et al.

(10) Patent No.: US 12,377,192 B2
(45) Date of Patent: Aug. 5, 2025

(54) TISSUE DERIVED POROUS MATRICES AND METHODS FOR MAKING AND USING SAME

(71) Applicant: Musculoskeletal Transplant Foundation, Edison, NJ (US)

(72) Inventors: Christopher M. Nichols, Tacoma, WA (US); Abigail Phipps, East Brunswick, NJ (US); Andrew Madans, Jersey City, NJ (US); Kevin Wu, Morganville, NJ (US); Evangelia Chnari, Scotch Plains, NJ (US)

(73) Assignee: Musculoskeletal Transplant Foundation, Edison, NJ (US)

( * ) Notice: Subject to any disclaimer, the term of this patent is extended or adjusted under 35 U.S.C. 154(b) by 450 days.

(21) Appl. No.: 17/603,448

(22) PCT Filed: May 8, 2020

(86) PCT No.: PCT/US2020/032022
§ 371 (c)(1),
(2) Date: Oct. 13, 2021

(87) PCT Pub. No.: WO2020/227601
PCT Pub. Date: Nov. 12, 2020

(65) Prior Publication Data
US 2022/0280693 A1 Sep. 8, 2022

Related U.S. Application Data

(60) Provisional application No. 62/845,015, filed on May 8, 2019.

(51) Int. Cl.
| | |
|---|---|
| A61L 27/36 | (2006.01) |
| A61L 15/40 | (2006.01) |
| A61L 15/42 | (2006.01) |
| A61L 27/54 | (2006.01) |
| A61L 27/56 | (2006.01) |
| A61L 27/58 | (2006.01) |
| A61L 27/60 | (2006.01) |
| A61M 1/00 | (2006.01) |

(52) U.S. Cl.
CPC .......... *A61L 27/3633* (2013.01); *A61L 15/40* (2013.01); *A61L 15/425* (2013.01); *A61L 27/362* (2013.01); *A61L 27/3687* (2013.01); *A61L 27/54* (2013.01); *A61L 27/56* (2013.01); *A61L 27/58* (2013.01); *A61L 27/60* (2013.01); *A61M 1/915* (2021.05); *A61L 2430/40* (2013.01)

(58) Field of Classification Search
None
See application file for complete search history.

(56) References Cited

U.S. PATENT DOCUMENTS

| | | | |
|---|---|---|---|
| 5,636,643 A | 6/1997 | Argenta et al. | |
| 5,645,081 A | 7/1997 | Argenta et al. | |
| 8,163,974 B2 | 4/2012 | Ambroio et al. | |
| 8,197,806 B2 | 6/2012 | Girouard et al. | |
| 9,642,937 B2 | 5/2017 | Zhao et al. | |
| 10,039,633 B2 | 8/2018 | Ansorge et al. | |
| 10,213,526 B2 | 2/2019 | Badylak et al. | |
| 10,869,949 B2 | 12/2020 | Zelen et al. | |
| 11,638,640 B2 | 5/2023 | Rehnke | |
| 11,992,579 B2 | 5/2024 | Valmikinathan et al. | |
| 2005/0266390 A1* | 12/2005 | Ueda et al. ............... | A61F 2/06 435/1.1 |
| 2007/0299412 A1 | 12/2007 | Vogel | |
| 2011/0195107 A1 | 8/2011 | Min et al. | |
| 2011/0251566 A1 | 10/2011 | Zmnitsky et al. | |
| 2012/0310367 A1 | 12/2012 | Connor | |
| 2014/0163447 A1 | 6/2014 | Wieland et al. | |
| 2015/0283287 A1 | 10/2015 | Agarwal et al. | |

(Continued)

FOREIGN PATENT DOCUMENTS

| | | |
|---|---|---|
| AU | 2020267589 | 1/2022 |
| CA | 3138899 | 11/2020 |

(Continued)

OTHER PUBLICATIONS

Grabow, N., et al., Artificial Organs 28(11): 971-979 (2004). (Year: 2004).*
First Examination Report issued on Jan. 16, 2024 by the Canadian Patent Office in connection with corresponding Canadian Patent Application No. 3,138,899.
International Search Report issued on Jul. 31, 2020 for corresponding International Patent Application No. PCT/US2020/032022.
Written Opinion of the International Search Authority issued on Jul. 31, 2020 for corresponding International Patent Application No. PCT/US2020/032022.
International Preliminary Report on Patentability for corresponding International Patent Application No. PCT/US2020/032022.

(Continued)

*Primary Examiner* — David J Blanchard
*Assistant Examiner* — Daniel F Coughlin
(74) *Attorney, Agent, or Firm* — Cole Schotz P.C.; Marcella M. Bodner, Esq.

(57) ABSTRACT

Tissue derived porous matrices for treating wounds are provided, as well as methods for making and using them. The tissue derived porous matrices comprise processed tissue of any of several types, such as dermis, adipose, etc., and have a plurality of interconnected pores which allow fluid flow through the matrices. The tissue derived matrices are biocompatible resorbable matrices which remodel with native tissue and facilitate and enhance cell infiltration and tissue ingrowth into the matrices during the wound healing process, thereby enhancing wound healing and tissue remodeling when implanted into a patient. The tissue derived matrices are useful with reduced or negative pressure wound healing methods and systems, without the need to repeatedly revisit the treatment site and remove previously implanted matrices.

14 Claims, 6 Drawing Sheets

(56) References Cited

U.S. PATENT DOCUMENTS

| | | | |
|---|---|---|---|
| 2015/0352257 A1* | 12/2015 | Early | A61L 27/3687 |
| | | | 435/378 |
| 2016/0051728 A1 | 2/2016 | Flynn | |
| 2016/0101215 A1 | 4/2016 | Zhao et al. | |
| 2018/0326120 A1 | 11/2018 | Grant et al. | |
| 2019/0374683 A1 | 12/2019 | Badylak et al. | |
| 2020/0000965 A1* | 1/2020 | Klopotek | A61L 27/3641 |
| 2020/0376160 A1 | 12/2020 | Xu et al. | |
| 2023/0211048 A1 | 7/2023 | Xu et al. | |
| 2024/0342341 A1 | 10/2024 | Valmikinathan et al. | |

FOREIGN PATENT DOCUMENTS

| | | | |
|---|---|---|---|
| CN | 106310373 | | 1/2017 |
| CN | 106730008 | | 5/2017 |
| CN | 106880872 | | 6/2017 |
| DE | 10350654 | | 6/2005 |
| EP | 3965835 | | 3/2022 |
| EP | 3965835 | B1 | 9/2024 |
| IL | 287906 | | 1/2022 |
| JP | 2009504246 | | 2/2009 |
| JP | 2016521592 | | 7/2016 |
| JP | 2018127490 | A | 8/2018 |
| JP | 2022531489 | | 7/2022 |
| JP | 2022531489 | A | 7/2022 |
| KR | 20100041027 | A | 4/2010 |
| KR | 20220018481 | | 2/2022 |
| WO | 2004104076 | | 12/2004 |
| WO | 2005113656 | | 12/2005 |
| WO | 2008020066 | | 2/2008 |
| WO | 2014110269 | | 7/2014 |
| WO | 2020227601 | | 11/2020 |

OTHER PUBLICATIONS

Choi, et al., "Full-thickness skin wound healing using human placenta-derived extracellular matrix containing bioactive molecules", Tissue Engineering Part A, 2013, vol. 19, pp. 3290339.
EP Communication pursuant to Article 94(3) EPC issued on Sep. 26, 2022 for corresponding European Patent Application No. 20728625.3.
Second Written Submissions filed Feb. 16, 2024, in advance of Oral Hearing for May 16, 2024, in the corresponding European Patent Application No. 20728625.3.
Office Action issued by the Israeli Patent Office on Feb. 21, 2024 in connection with corresponding Israeli Patent Application No. 287906.
English translation of Office Action issued by the Israeli Patent Office on Feb. 21, 2024 in connection with corresponding Israeli Patent Application No. 287906.
Second Examination Report issued on Feb. 15, 2023 by the Australian Patent Office for Australian Patent Application No. 2020267589.
Third Australian Examination Report issued on Sep. 28, 2023 for corresponding Australian Patent Application No. 2020267589.
First Office Action issued on Feb. 7, 2024 by the Japanese Patent Office for corresponding Japanese Patent Application No. 2021-566098.
EP Communication regarding oral proceedings issued on Nov. 27, 2023 for corresponding European Patent Application No. 20728625.3.
EP Communication regarding summons for oral proceedings, issued on Apr. 19, 2023 for corresponding European Patent Application No. 20728625.3.
EP Communication regarding oral proceedings issued on Dec. 8, 2023 for corresponding European Patent Application No. 20728625.3.
EP Communication regarding summons for new oral proceedings issued on Dec. 21, 2023 for corresponding European Patent Application No. 20728625.3.
Notice of Acceptance issued on Dec. 13, 2023 for corresponding Australian Patent Application No. 2020267589.
Machine Translation from German of DE 10350654 A1 (Abstract, Description, Claims), filed Oct. 29, 2003, published Jun. 2, 2005.
Meyer M., "Processing of collagen based biomaterials and the resulting materials properties", Meyer BioMed Eng OnLine, 2019, vol. 18, pp. 1-74.
Third Examination Report issued Sep. 28, 2023 for corresponding Australian Patent Appln No. 2020267589 (OEE Work Product for PPH).
First Examination Report for Australian Patent Application No. 2020267589, issued on Dec. 22, 2022.
Australian Patent No. 2020267589, granted on Apr. 18, 2024 for corresponding Australian Patent Application No. 2020267589, previously cited . . . .
English Translation Office Action issued on Jun. 7, 2024 for corresponding Japanese Patent Application No. 2021-566098.
Office Action issued on Jun. 7, 2024 for corresponding Japanese Patent Application No. 2021-566098.
English Translation Korean Intellectual Property Office, Notice of Preliminary Rejection issued on Jun. 4, 2024, for corresponding Korean Patent Application No. 10-2021-7038783.
Korean Intellectual Property Office, Notice of Preliminary Rejection issued on Jun. 4, 2024, for corresponding Korean Patent Application No. 10-2021-7038783.
Provision of minutes in accordance with Rule 124(4) EPC, Part 1, in connection with corresponding European Patent Application No. 20728625.3.
Provision of minutes in accordance with Rule 124(4) EPC, Part 2, in connection with corresponding European Patent Application No. 20728625.3.
Communication under Rule 71(3) EPC issued by the European Patent Office on Jun. 11, 2024 in connection with corresponding European Patent Application No. 20728653.3.
Translation of Notice of Acceptance issued on Oct. 7, 2024 for corresponding Israeli Patent Application No. 287906.
Notice of Acceptance issued on Oct. 7, 2024 for corresponding Israeli Patent Application No. 287906.
Communication of the date of registration of unitary effect pursuant to Rule 7(1) UPR, issued on Oct. 23, 2024 for corresponding European Patent Application No. 20728625.
Notice of Final Rejection issued on Oct. 31, 2024 for corresponding Korean Patent Application No. 10-2021-7038783.
English translation of Notice of Final Rejection issued on Oct. 31, 2024 for corresponding Korean Patent Application No. 10-2021-7038783.
Certificate of Patent Grant for JP Pat. No. 7551632 (Japanese language), issued Sep. 6, 2024, for co-owned corresponding Japanese Pat. Appln. No. 2021-0377815.
English Translation of Certificate of Patent Grant for JP Pat. No. 7551632 (Japanese language), issued Sep. 6, 2024, for co-owned corresponding Japanese Pat. Appln. No. 2021-0377815.
English translation of Decision to Grant. Issued by Japanese Patent Office on Aug. 9, 2024 for corresponding Japanese Patent Application No. 2021-566098.
Decision to Grant. Issued by Japanese Patent Office on Aug. 9, 2024 for corresponding Japanese Patent Application No. 2021-566098.
Notice of Allowance issued by the Canadian Patent Office on Jun. 10, 2024 for corresponding Canadian Patent Application No. 3,138,899.

* cited by examiner

Test chamber diagram with ports

System diagram of simulated NPWT system connections

TISSUE DERIVED POROUS MATRICES AND METHODS FOR MAKING AND USING SAME

CROSS-REFERENCE TO RELATED APPLICATIONS

The present application is the national stage of International Patent Application No PCT/US2020/032022, filed May 8, 2020, which claims the benefit of U.S. Provisional Application No. 62/845,015, filed on May 8, 2019, the entire disclosures of both of which are hereby incorporated by reference herein.

FIELD OF THE INVENTION

The present invention relates generally to tissue derived porous matrices useful for treating wounds. More particularly, the present invention relates to biocompatible resorbable matrices useful as wound dressings or grafts and which are derived from donor tissue and have pores for enhancing wound healing and tissue remodeling when implanted into a patient.

BACKGROUND OF THE INVENTION

Wound treatment and healing have been studied for centuries. As the understanding of the body's healing mechanisms has increased, more effective techniques for enhancing and accelerating wound healing have been developed. Various techniques employed to enhance and accelerate wound healing include: irrigating and/or debriding the wound to remove debris, toxins and bacteria; removing excess fluids; supplying local and systemic antibiotics and anesthetics; applying a scaffold (e.g., natural, biologic, synthetic, etc.) to the wound to provide a substrate for new tissue growth; providing cells, growth factors or other proteins to the wound; and supplying other tissue supportive therapies such as cells, growth factors and other proteins, to the wound site. Combinations of such techniques are often applied to enhance wound healing.

Reduced (i.e., negative, subatmospheric, hypobaric, etc.) pressure therapy is a successful technique for promoting and enhancing wound healing in soft tissue wounds that are slow, or fail, to heal completely. Reduced pressure therapy, sometimes referred to as vacuum assisted closure (or "V.A.C."), generally involves application of a reduced pressure, i.e., less than the ambient pressure, at the wound site with a magnitude and for a time period sufficient to promote healing and/or tissue growth. It is believed that the reduced pressure applied to a wound site assists in increasing perfusion of blood/oxygen and flow of fluids, evacuation of wound exudates, and migration of epithelial tissue towards and formation of new subcutaneous tissue in the wound site. When coupled with an open lattice sponge (e.g., having interconnected pores), reduced pressure wound therapy techniques also confer both macrostrain and microstrain (and microdeformation) to the area of tissue loss with significant well described wound healing benefits. These beneficial effects include, but are not limited to: mechanical reduction of the wound size through tissue creep and stress relaxation and tissue expansion of the periwound tissues (macrostrain) as well as microstrain which subjects the healing cells to microdeformation that potentiates and upregulates a number of beneficial cellular healing processes. Reduced pressure therapy may be used alone, or in combination with any of the aforesaid wound treatment techniques.

Reduced pressure therapy systems and methods generally involve placement of a dressing on or in a wound site, followed by application of reduced pressure to the wound site using a reduced pressure source in fluid communication with the wound site through the dressing. The dressing serves as a manifold which distributes the reduced pressure throughout the wound site, thereby promoting the flow and migration of fluids, epithelial tissue and subcutaneous tissue from healthy tissue into the wound site.

Dressings suitable for performing reduced pressure therapy generally include at least a porous component and a semipermeable (i.e., semiocclusive or impervious) barrier component, where the porous component is positioned, partially or fully, in direct contact with the wound site, often filling the wound site, and the semipermeable barrier component is positioned to cover the entire wound site, including the porous component. The semipermeable barrier component tends to have a sheet-like shape and is sealingly affixed about its perimeter to the wound site. A conduit, which passes through the semipermeable barrier component of the dressing and onto the porous component, provides fluid/air and pressure communication between the reduced pressure source and the wound site, through the dressing.

Early embodiments of devices and methods for practicing reduced pressure therapy are described in U.S. Pat. Nos. 5,636,643 and 5,645,081, the disclosures of which are hereby fully incorporated herein by reference. Such early versions utilized dressings with a porous component made of materials which were not bioresorbable or remodelable in vivo with biological tissues, or were only partially so. This necessitated removal of the porous component from the wound site prior to complete healing. Furthermore, as part of the healing process, there was often tissue ingrowth which at least partially infiltrated the porous component so that, when it was removed, new and/or healthy tissue were also removed or damaged, thereby causing additional trauma to the wound site during healing and pain to the patient. For larger or deeper wound sites, removal and replacement of the porous component with a fresh new porous component (e.g., of a smaller size or different shape which better fit the partially healed wound site) would be performed repeatedly, resulting in ongoing damage and trauma to the wound site, thereby potentially slowing or retarding the healing progress. Further it has been identified that the use of non-resorbable foams have a risk for erosion when used in placement next to vital organs, nerves, or blood vessels.

Improved devices and methods for practicing reduced pressure therapy, in which at least a portion of the porous component comprises a resorbable material providing scaffold for new tissue ingrowth which need not be removed, were developed. Several such improved devices and methods are described in U.S. Pat. Nos. 8,163,974 and 8,197,806, the disclosures of which are also hereby fully incorporated herein by reference.

More particularly, U.S. Pat. No. 8,163,974 describes modified dressings for use with reduced pressure therapy. One embodiment is a dressing which includes an open-cell foam pad, which is conventionally non-bioresorbable, with a bioresorbable cell-growth enhancing matrix implanted or superimposed thereon. U.S. Pat. No. 8,163,974 discloses several bioresorbable materials suitable for the bioresorbable matrix, and even that, in a particular embodiment, the open-cell foam pad and the bioresorbable matrix may both be made of a bioresorbable branched polymer. Additionally, U.S. Pat. No. 8,163,974 discloses another improved dressing comprising a non-bioabsorbable porous manifold component and a bioabsorbable porous scaffold component which is placed in contact with the wound site and facilitates cell infiltration and tissue ingrowth. This dressing also includes an intermediate release layer positioned in between the manifold and scaffold components and made of a "release" material which serves as a barrier to tissue ingrowth into the manifold component and dissolves upon hydration, thereby facilitating separation of the manifold component from the non-bioabsorbable porous manifold component. None of the bioresorbable materials disclosed for use in making any components of the dressings described in U.S. Pat. No. 8,163,974 are tissues or derived from tissues recovered from donors. The pores of the bioabsorbable porous scaffold component described in U.S. Pat. No. 8,163,974 have pore sizes typically between about 50 and 500 microns, and more preferably between about 100 and 400 microns. Pore sizes below 50 microns tend to inhibit or prevent tissue ingrowth. In one embodiment, the preferred average pore size of pores within the scaffold is about 100 microns.

U.S. Pat. No. 8,197,806 discloses a modified dressing purported to stimulate cartilage formation at tissue site when employed with reduced pressure therapy. More particularly, the dressing of U.S. Pat. No. 8,197,806 is described as having a porous manifold component for distributing reduced pressure to a tissue site and a porous scaffold for placement adjacent to the tissue site. A chondrocyte and/or cytokine is also provided either directly to the tissue site or within the porous scaffold component. U.S. Pat. No. 8,197,806 provides that either or both of the manifold and scaffold materials may be made of bioresorbable materials, and also that the scaffold component may be made of any of several synthetic and natural polymer materials, including processed allograft material, using any polymer processing techniques such as melt-spinning, extrusion, or casting. The pores of the bioresorbable porous scaffold component of the dressings described in U.S. Pat. No. 8,197,806 have pore sizes ranging between 25 and 500 microns, such as between 50 and 250 microns, or between 50 and 150 microns.

Further improvements to the dressings useful for treatment of wound sites to enhance healing and, particularly, for use with reduced pressure therapy, would be welcomed by patients and practitioners. For example, modified wound dressings having enhanced ability to promote effective and efficient wound healing, such as through improved and/or accelerated cell infiltration, proliferation, growth and activity continue to be sought.

SUMMARY OF THE INVENTION

The invention described and contemplated herein relates to a tissue derived porous matrix comprising a decellularized tissue, wherein the matrix is resorbable and has a plurality of interconnected pores which allow fluid flow through the matrix. When the matrix is implanted, in contact or proximity, with a wound site of a subject, the matrix at least partially degrades, partially remodels with native tissue at the wound site, or both, wherein no portion of the matrix need be removed from the wound site after being positioned with the wound. When implanted in proximity or contact with a wound site of a subject, fluid flow from the wound site and through the matrix occurs, with or without application of reduced pressure, during healing at the wound site.

In some embodiments, a biocompatible composition is provided which comprises the foregoing tissue derived porous matrix and one or more additional biocompatible materials.

A method for producing a tissue derived porous matrix is also provided, wherein the matrix is resorbable and has a plurality of interconnected pores which allow fluid flow through the matrix, the method comprising the steps of: (A) obtaining a sample of tissue; (B) optionally, reducing the size of the tissue; (C) optionally, delipidating or demineralizing the tissue; (D) decellularizing the tissue; (E) optionally, disinfecting the tissue; (F) optionally, combining a solvent with the tissue; (G) optionally, placing the tissue in a container or mold; (H) forming or modifying pores; (I) optionally, drying the tissue; (J) optionally, crosslinking or other stabilizing of the tissue; (K) optionally, drying the crosslinked tissue; and (L) optionally, disinfecting the crosslinked tissue. In some embodiments of the method, the tissue comprises one or more tissue types selected from dermis, placental, adipose, fascia, and combinations thereof.

In some embodiments of the method for producing a tissue derived porous matrix, the step of disinfecting the tissue (E) comprises sterilizing the tissue, either before or after the drying step (I), or both. In some embodiments of the method, the step of combining a solvent with the tissue (F) is performed prior to the drying step (I) and the solvent is water, wherein a tissue and water mixture is formed, and wherein the steps of forming or modifying pores (H) and drying the tissue (I) are performed concurrently by lyophilizing the tissue and water mixture. In some embodiments of the method, the method further comprises the step of formulating, by mixing, attaching, or otherwise combining, the tissue derived porous matrix with other materials or other synthetic or naturally-derived matrices.

A method for treating a wound is also provided which comprises implantation of a tissue derived porous matrix, in contact or proximity, with a wound site of a subject, wherein the matrix comprises a tissue having a plurality of interconnected pores which allow fluid flow through the matrix and the matrix is resorbable.

In some embodiments, when a portion of the tissue derived porous matrix has not been resorbed some period of time after implantation, the method for treating a wound may further comprise removing at least a portion of un-resorbed portions of the matrix from the wound site in a subsequent procedure. The period of time after implantation may be at least about 7 days. In some embodiments, the decellularized tissue is derived from one or more tissue types selected from dermis, placental, adipose, fascia, and combinations thereof.

A wound dressing is also provided which comprises a porous component comprising the foregoing tissue derived porous matrix; and an semipermeable barrier component sized and shaped to cover the porous component and a wound site to be treated with the wound dressing.

Another method for treating a wound which uses the foregoing wound dressing, comprises: placing of the porous component, in contact or proximity, with a wound site of a subject; placing the semipermeable barrier component over the porous component such that it covers the porous component and the wound; sealingly affixing the semipermeable barrier component to healthy tissue about a perimeter of the wound to create a pocket of limited permeability; and applying reduced pressure to the to the pocket and causing fluid to flow from the wound, through the tissue derived porous matrix, and out of the pocket.

BRIEF DESCRIPTION OF THE DRAWINGS

The present invention will be further explained with reference to the attached drawings, in which.

DETAILED DESCRIPTION OF THE INVENTION

Figure 1:
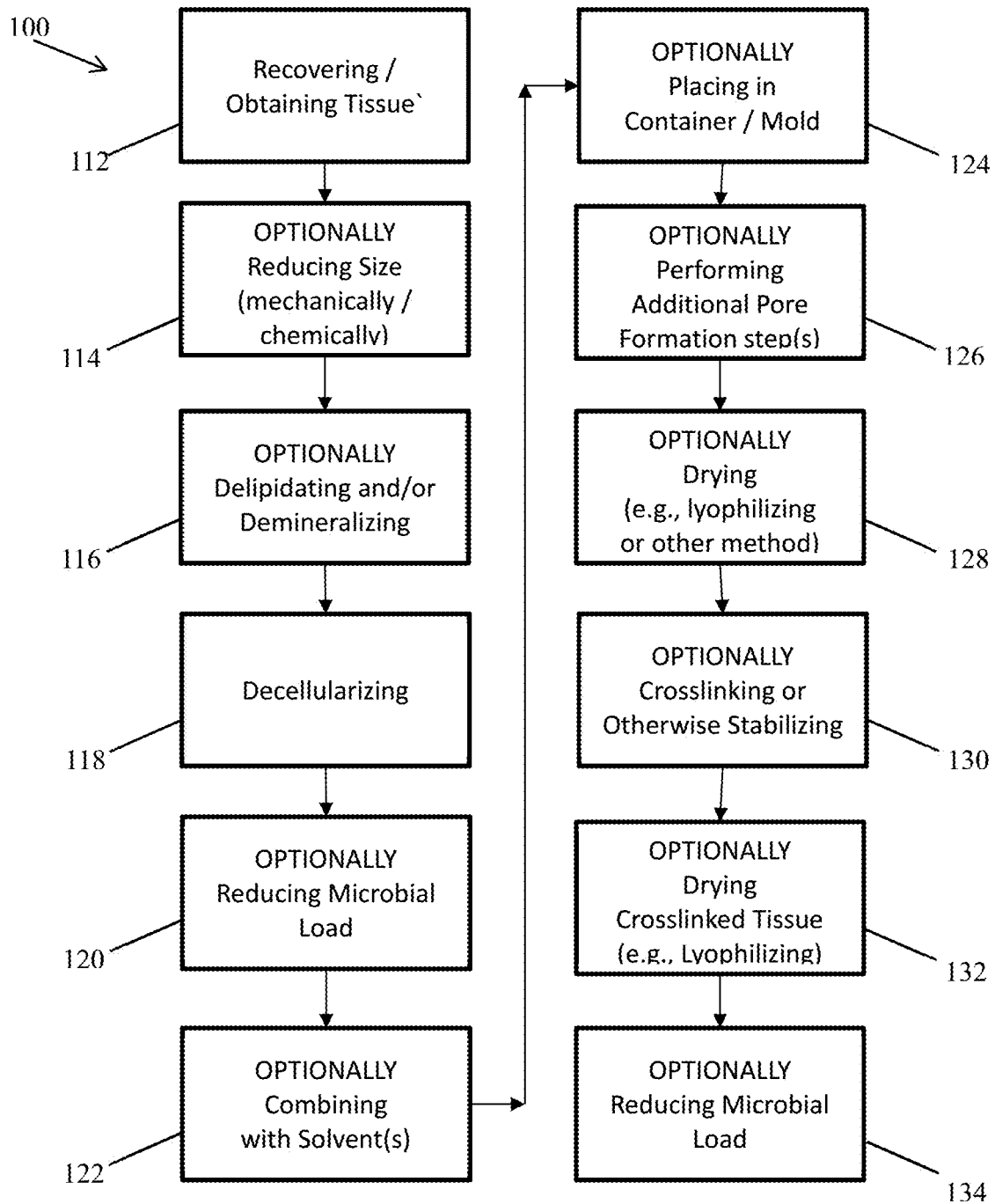
FIG. 1 is a flowchart showing the basic steps in an exemplary method for producing tissue derived porous matrices in accordance with the present invention.

Detailed descriptions of one or more embodiments of the present invention are disclosed herein. It should be understood that the disclosed embodiments are merely illustrative of the invention which may be embodied in various forms. In addition, each of the examples given in connection with the various embodiments of the invention is intended to be illustrative, and not restrictive. Further, the figures are not necessarily to scale, and some features may be exaggerated to show details of particular components. In addition, any measurements, specifications and the like shown in the figures are intended to be illustrative, and not restrictive. Therefore, specific structural and functional details disclosed herein are not to be interpreted as limiting, but merely as examples for teaching one skilled in the art to variously employ the present invention.

The tissue derived porous matrices described and contemplated herein (also referred to below as "biosponges") enhance wound healing when applied to a wound site because, being porous, they provide a three dimensional scaffold for tissue ingrowth while allowing escape of excess fluid from the wound site. The porous matrices described and contemplated herein have a lattice of pores and are compressible. This compressible nature and the lattice of pores will confer macrostrain and microstrain, respectively. These forces are known to improve the rate and quality of wound healing and, thus, are expected contribute to rapid de novo tissue ingrowth into the tissue derived porous matrix. Since they are tissue derived, the porous matrices are also biocompatible and at least partially remodel into native tissue, which means it is not necessary to remove or replace them after initial placement at the wound site, thus avoiding damage to newly formed tissue during the healing process, as well as additional manipulation, pain, risk of procedures to the patient. Reducing the need to repeatedly revisit a treatment site to remove previously implanted matrices will provide a more convenient, comfortable, and less resource (e.g., inpatient or outpatient nursing care, home health care, other health or personal care provider, etc.) intensive course of therapy for the patient. This benefit is achieved even in embodiments where the tissue derived matrices are only partially absorbed or remodeled into native tissue, because only smaller remaining portions of tissue derived matrices would need to be removed from the treatment site, if at all. In some embodiments, the tissue derived porous matrices are acellular and, therefore, lack immunogenicity and are highly biocompatible. Additionally, the tissue derived porous matrices will provide needed bulk, support, barrier function, and padding, for subjects having experienced prior tissue loss and/or destruction, regardless of the cause. The aforesaid characteristics and benefits also make the tissue derived porous matrices useful as dressings for reduced pressure wound therapy.

The tissue derived porous matrices may also comprise a small or significant percentage of additional biocompatible materials, such as without limitation, biocompatible non-tissue material, including but not limited to polymers (natural or synthetic), ceramics, metals, nature-derived or animal-derived biomaterials, more specifically between 20 and 80%. The tissue derived porous matrices may also contain endogenous beneficial substances such as growth factors, extracellular matrix components, nutrients, biologically active molecules, vitamins, or integrins which facilitate various tissue healing and remodeling mechanisms including, without limitation, extracellular matrix production and deposition, cell infiltration and proliferation, pathogen barrier and reduction, and angiogenesis. Furthermore, the tissue derived porous matrices may be coated with, infused with, or otherwise include exogenous substances or materials, including without limitation, cells, growth factors, extracellular matrix components, nutrients, integrins, anti-microbial agents, anti-infective agents, bacteriostatic agents, or other substances such as, but not limited to, those which promote cell migration, attachment, proliferation, growth and activity. For example, without limitation, some growth factors are known and/or believed to expedite cell recruitment, modulate inflammation, etc. Methods for making the tissue derived porous matrices and using them for wound treatment are also described herein below.

While the aforesaid tissue derived porous matrices will be described in detail hereinafter as a particular embodiment useful for performing reduced pressure therapy wound treatment, it is not limited to such embodiments and uses. Rather, persons of ordinary skill will recognize that the tissue derived porous matrices are useful as dressings, grafts, scaffolds, etc., applied to wound sites and will facilitate and enhance wound healing even in the absence of reduced pressure therapy. Such uses generally include placement (i.e., implantation) of a tissue derived porous matrix, as described and contemplated herein, in contact or proximity, with a wound site of a subject wherein the matrix is resorbable and has a plurality of interconnected pores which allow fluid flow through the matrix. Such implantation of the tissue derived porous matrices allow and facilitate fluid flow from the wound site and through the matrix, with or without application of reduced or negative pressure, during healing at the wound site. Additionally, the tissue derived porous matrices described and contemplated herein are useful for treatment of a subject to restore, enhance, add to, or replace tissues in any area of the subject's body that requires support, restoration, regeneration, enhancement, or replacement.

In some embodiments, at least a portion of the tissue derived porous matrix will be resorbed some period of time after implantation (e.g., at least about 7 days, or at least about 14, or at least about 21 days, or at least about 6 weeks, or at least about 10 weeks, or up to about 3 months, etc.) at a wound site. In some embodiments, when a portion of the tissue derived porous matrix has not been resorbed some period of time after implantation (at the discretion of the medical professional treating the wound site), at least a portion (i.e., some or all) of such un-resorbed portions may be removed from the wound site in a subsequent debridement procedure, e.g., similar to debridement of native endogenous tissue in a wound or autograft. Additionally, in some embodiments such un-resorbed portions may not be removed from the wound site, but rather, will remain implanted at the wound site. Whether or not to remove un-resorbed portions of an implanted tissue derived porous matrix is well within the ability and discretion of persons of ordinary skill in the relevant art (e.g., medical professionals). In some embodiments, at the discretion of persons of ordinary skill in the relevant art (e.g., medical professionals), at least a portion of un-resorbed tissue derived porous matrix may be removed from a wound site at any time after implantation (i.e., even earlier than about 7 after implantation), regardless of whether any portion (or none) of the matrix has been resorbed.

Furthermore, in some embodiments, treatment of a wound (or wound site) of a subject using tissue derived porous matrices may comprise: a first implantation (placement in contact or proximity with the wound) of a first tissue derived porous matrix in a subject, and a second implantation (placement in contact or proximity with the wound) of a second tissue derived porous matrix some period of time after the first implantation. In fact, some embodiments of methods for using the matrices described and contemplated herein may comprise multiple implantations of multiple such matrices at or near a wound of a subject. In some embodiments, treatment of a wound using tissue derived porous matrices may comprise: a first implantation (placement in contact or proximity with a wound site of a subject) of two or more tissue derived porous matrices in a subject. The two of more matrices may be implanted concurrently, sequentially, or a combination of both. As will be readily understood by persons of ordinary skill in the relevant art, further variations and combinations of the foregoing uses of the presently described and contemplated tissue derived porous matrices are possible and useful. As used herein, the term "about" as applied to a period of time after implantation means 18 hours.

The terms "wound" and "wound site" as used herein mean a place or location in or on a body where tissue has been damaged, lost or degenerated such as by trauma, injury, disease, infection, surgical procedure (e.g., resection, etc.) and the like. Several diseases, traumas, injuries and surgical procedures result in one or more of damage to, loss of, or degeneration of body tissue, thereby resulting in formation of wound sites, which may be located externally, internally, or both. For example, surgical removal of soft tissue tumors and masses often result in the loss of bulk tissue. Other surgical and cosmetic procedures can, to varying degrees, cause tissue damage, loss and/or degeneration which may impair functionality as well as aesthetic appearance. Tissue damage, loss or degeneration can also result from trauma, such as from blunt force impacts and weapon injuries, including accidental and intentional. Finally, several diseases, including acute and chronic infection and wasting disease, may cause significant damage to, loss of and/or degeneration of body tissue. Any place where body tissue has been damaged, lost and/or degenerated by any and all such circumstances and events are intended to be included, without limitation, within the meaning of "wound" and "wound site."

The terms "healing" and "wound healing" as used herein mean the process by which damaged, missing or degenerated tissue is repaired and or replaced by new tissue. Wound healing is currently understood to involve three general phases: inflammation, proliferation, and maturation. These phases tend to occur sequentially, but also often overlap with one another. An initial "inflammatory" phase, involving hemostasis and inflammation, is most often the body's reaction to tissue injury or damage. This is followed by a second phase during which epithelialization, angiogenesis, granulation tissue formation, and collagen deposition typically occur. The last phase tends to consist of maturation and tissue remodeling. The three step wound healing process is actually more complex than the aforesaid description would seem to indicate, but is generally accurate for most wounds, including superficial, deep and chronic wounds, when complete healing does occur. Wound healing is affected and often complicated by local factors such as ischemia, edema, and infection, as well as systemic factors including, for example, diabetes, age, hypothyroidism, malnutrition, and obesity.

The term "angiogenesis" as used herein means the origination and development (i.e., growth) of new blood vessels, which typically begins with migration of endothelial cells and formation of new capillary blood vessels. Angiogenesis is necessary to meet the increasing metabolic requirements of new and existing tissue growth and enlargement, so that such tissue has an adequate blood supply for providing oxygen, nutrients and waste drainage. This process is essential for healing, growth, development, and maintenance of body tissues.

The rate limiting step of wound healing is often angiogenesis. In wound healing, angiogenesis is achieved by endothelial cell migration and sprouting of capillaries into a wound bed is critical to the regeneration of tissue at the wound site. Granulation and tissue formation are enabled and supported at the wound site by the nutrients supplied by such capillaries. Impairments in wound angiogenesis therefore may lead to chronic non-healing wounds.

Expression of the angiogenic phenotype is a complex process that requires a number of cellular and molecular events to occur in sequential steps. Some of these activities include endothelial cell proliferation, degradation of surrounding basement membrane, migration of endothelial cells through the connective tissue stroma, formation of tube-like structures, and maturation of endothelial-lined tubes into new blood vessels (inosculation). Angiogenesis is controlled by positive and negative regulators. In addition to endothelial cells, cells associated with tissue repair, such as platelets, monocytes, and macrophages, release angiogenic growth factors, such as vascular endothelial growth factor (VEGF) into injured sites that initiate angiogenesis.

The term "scaffold" as used herein refers to a substance or structure used to enhance or promote the growth of cells and/or the formation of tissue. In the present context of wound treatment and healing, a scaffold is typically a three dimensional porous structure that provides a template for cell growth.

The term "tissue derived" as used herein to describe the porous matrices means that they comprise processed tissue produced by recovering tissue from one or more donors and treating the recovered tissue to remove blood, debris, bioburden, a majority of the endogenous cells and cellular material, so they essentially lack immunogenicity while retaining a proportion of the initially present, naturally formed physical structure of the tissue sufficient to provide a three-dimensional scaffold capable of infiltration by cells and ingrowth by new tissue. A "majority of the endogenous cells and cellular material" means greater than about 50%, by weight (wt %), of the cellular DNA material, based on the total weight of the cellular DNA material initially present in the recovered tissue before processing. The recovered tissue may be autogeneic (i.e., recovered from the same individual as the intended recipient), allogeneic (i.e., recovered from a different individual of the same species as the intended recipient), or xenogeneic (i.e., recovered from an individual of a different species as the intended recipient). Furthermore, the recovered tissue may be adipose, fascia, dermis, bone, cartilage/meniscus, muscle, tendon/ligament, placenta (including amnion, chorion, aminochorion, Wharton's jelly, and umbilical cord), placental disk, and combinations thereof.

As used herein, the term "porous" as used to describe the tissue derived matrices means that the matrices have a plurality of interconnected pores (i.e., small holes, interstices, cells, cavities or openings), at least a portion of which are in fluid communication with one another such that they allow fluid to flow therethrough and, therefore, also through the matrices. The pores also facilitate and enhance cell infiltration and tissue ingrowth into the matrices during the wound healing process. The size, shape, or interconnectivity of the pores may be uniform, random, or patterned, and may be modified to enhance or control one or more processes such as, without limitation, new tissue formation, tissue remodeling, cell infiltration and proliferation, angiogenesis, and host integration.

As will be readily understood and practicable by persons of ordinary skill in the relevant art, varying the size and shape of the pores, as well as the porosity can produce variation and control of the flow characteristics of fluid passing through the tissue derived porous matrices. Generally, the tissue derived porous matrices described herein have an average pore size of from about 75 microns to about 1500 microns, such as from about 400 microns to about 600 microns.

Generally, the tissue derived porous matrices described herein have a porosity of from about 50% to about 99%, such as from about 80% to about 99%, or from about 80% to about 90%. This relatively high porosity should allow the attachment of infiltrating cells to induce new tissue formation, as well as allowing the pores to be seeded with cells of desired type in advance to promote formation of a desired tissue type.

The terms "resorbable," "absorbable" and "bioabsorbable" and their grammatical variants, are used herein interchangeably to describe matrices or grafts and means that the matrices or grafts, e.g., the material from which they are made, will at least partially degrade, remodel, or a combination of both, within a limited time period after implantation or placement in a biological environment, such as adjacent to, in contact with, or implanted in living tissue, which means that the matrices or grafts either do not need to be removed, or need to be only partially removed, after implantation or placement. In some embodiments, after that limited period of time, the matrix or graft is no longer recognizable as existing in its initial form such that only a portion or virtually no portion of the graft or matrix is present and/or recognizable. A resorbable matrix or graft may be resorbed by any of a variety of mechanisms. For example, without limitation, a resorbable matrix or graft may be resorbed through the action of cellular activity, such as through the action of macrophages that break down the resorbable regeneration matrix. A resorbable matrix or graft may be resorbed after being broken down by mechanical, chemical, metabolic and/or enzymatic degradation. It will be understood by persons of ordinary skill in the relevant art that the precise mechanism of resorbability is not critical, so long as the break down products of the regeneration matrix can be resorbed by and/or excreted from the body. The limited period of time for which a particular resorbable matrix or graft exists after placement or implantation in living tissue may be, for example without limitation, hours, days, weeks, months or even years. Typically, as also understood by persons of ordinary skill in the relevant art, such limited period of time will be determined by various factors including the type of biological environment and adjacent tissue, the size or mass of the resorbable matrix or graft that is implanted, the conditions present in the biological environment (temperature, pressure, pH, etc.), as well as the size, mass, density and other characteristics of the resorbable matrix or graft. For example, without limitation, the limited time period during which a resorbable matrix or graft may exist after implantation may be 1, 2, 3, 4, 5, 6, 7, 8, 9 10, 11, 12, 13, 14, 15, 16, 17, 18, 19, 20, 21, 22, 23, 24, 25, 30, 35, 40, 45, 50, 55, 60, 65, 70, 75, 80, 85, 90, 95, 100, 110, 120, 130, 140, 150, 160, 170, 180 days, or more, or any value therebetween, when placed in the biological environment. For example, it is believed that, as a practice application parameter, the limited time period during which a resorbable matrix or graft should exist after implantation is at least about 4-7 days to minimize the need for placement of additional dressings at the wound site (i.e., minimize dressing changes).

The term "reduced pressure" as used herein generally means a pressure less than the ambient pressure existing at a tissue site undergoing treatment. Most often, this reduced pressure will be less than the atmospheric pressure at which the patient is located and includes, without limitation, hypobaric, subatmospheric, and negative pressures. Similarly, the reduced pressure may be less than a hydrostatic pressure associated with tissue at the tissue site. Although the terms "vacuum" and "negative pressure" may be used herein to describe the pressure applied to a wound site, the actual pressure reduction applied may be significantly less than the pressure reduction normally associated with a complete vacuum. Reduced pressure may initially generate fluid flow in the wound site and surrounding tissue. As the hydrostatic pressure around the wound site approaches the predetermined desired reduced pressure, fluid flow may diminish or essentially cease, whereupon reduced pressure is maintained for some period of time. Unless otherwise indicated, values of pressure stated herein are gauge pressures. Similarly, references to increases in reduced pressure typically refer to a decrease in absolute pressure, while decreases in reduced pressure typically refer to an increase in absolute pressure.

The term "reduced pressure source" as used herein refers to any device, such as a vacuum pump, wall suction, etc., which is capable of producing a reduced pressure of from about −0.1 mm Hg to about −500 mm Hg and includes a flexible conduit for fluidly connecting to a wound dressing suitable for use to perform reduced pressure therapy for treating a wound. The reduced pressure source may operate continuously, or intermittently or cyclically such that there are alternating periods of application and non-application to the wound site. As will be understood by persons of ordinary skill in the relevant art, the reduced pressure source may also include sensors, processing units, alarm indicators, memory, databases, software, display units, and user interfaces that further facilitate the application of reduced pressure treatment to the wound site. Additionally, the reduced pressure source may have additional features and components, such as, without limitation, one or more additional inlets, outlets, or both, which are configured for connecting additional conduits for delivery of fluids to a wound site, such as for irrigation or instillation of the wound site, or flushing and cleaning of the reduced pressure source. The fluids may be any fluid suitable for accomplishing the intended purpose of delivering the fluid to the wound site (e.g., rinse, cleanse, perfusion) or to the reduced pressure source (e.g., rinse, cleanse, disinfect).

The term "semipermeable" as used herein to describe a component of dressings suitable for wound treatment methods, including but not limited to reduced pressure therapies, means a component having a generally sheet-like shape, capable of providing or forming a sufficiently air tight pocket (e.g., containing a wound/porous component complex) at a wound or other site to be treated with the dressing (i.e., water vapor may pass through) such that reduced or negative pressure applied to the pocket facilitates and promotes controlled removal of fluids from the wound or tissue site and surrounding tissues. As used herein, the characteristic of "semipermeable" includes both relatively impervious (i.e., nonporous or have low moisture vapor transmission) as well as semiocclusive (i.e., moisture or vapor permeable). The semipermeable component of such dressings is sealingly affixed about its perimeter to the wound site, thereby providing the pocket of limited permeability at the wound site for controlled application of reduced pressure, as described herein. Thus, while the semipermeable component of the dressings need not prevent passage of absolutely all fluids and other matter therethrough, as will be understood by persons of ordinary skill in the relevant art, the less permeable this component is, the more effective the application of reduced pressure at the wound site will be.

The term "impervious" as used herein to describe a component of dressings suitable for use with reduced pressure therapy means a component having a generally sheet-like shape and being at least only semi-permeable such that transmission of at least liquid fluids, and optionally also gases, therethrough is essentially prohibited.

The following description of embodiments of dressings suitable for performing reduced pressure therapy treatment techniques describe the dressings as including tissue derived porous matrices and a second component which is impervious. Nonetheless, it will be readily understood by persons of ordinary skill in the relevant art that the second component for such dressing may be semipermeable, for example without limitation semiocclusive, and that the degree of permeability (i.e., semipermeable, impervious, semiocclusive, etc.) is determinable by such skilled persons based on the type of wound or other tissue site to be treated using such dressings, with or without application of reduced pressure, and the desired outcome of such treatment.

Dressings suitable for performing reduced pressure therapy typically include at least a porous component and an impervious component, where the porous component is positioned, partially or fully, in direct contact with the wound site, often filling the wound site, and the impervious component is positioned to cover the entire wound site, including the porous component (and sometimes also a portion of the normal tissue surrounding the wound site). The impervious component of such dressings typically has a sheet-like shape (though this is not required) which is sized to extend beyond the edges of the wound site to completely cover wound site and porous component. The impervious component is sealingly affixed to healthy tissue about the wound perimeter or circumference using, for example without limitation, a biocompatible adhesive. This arrangement provides a region or pocket of limited and restricted permeability at the wound site for controlled application of reduced pressure to the wound site and healthy tissues adjacent thereto. Preferably, the impervious component is made of an impermeable substance that is flexible and permits the diffusion of water vapor (preventing vapor-lock) but provides an air-tight enclosure.

A reduced pressure source is affixed in fluid communication with the dressing and wound site via a conduit which passes through (or under) the impervious component and at least partially onto, or in contact or proximity with, the porous component of the dressing. As will be recognized by persons of ordinary skill, while an opening may be provided through the impervious barrier component to allow passage of a conduit and permit fluid communication between the wound site and the external environment (and/or a reduced or negative pressure source), the conduit could also be passed underneath the impervious component and the impervious component sealingly affixed to the wound site and the conduit with the conduit held against the subject proximate the wound site in a manner which minimizes fluid flow or seepage around the conduit. While the amount and nature of reduced pressure applied to a tissue site will typically vary according to the application, permeability of the semipermeable component, and other factors familiar to persons of ordinary skill in the relevant art, the reduced pressure will typically be between −5 mm Hg and −500 mm Hg and more typically between −50 mm Hg and −200 mm Hg. The particular protocol used in reduced pressure treatment depends upon the location of the wound site, the reduced pressure dressing, and any pharmacological agents being utilized. Additionally, reduced pressure may be a substantially continuous or cyclical application such that it oscillates the pressure over time.

Generally, the dressing may have the porous and semipermeable components already assembled, joined or integrally formed together, with or without other additional optional components, prior to placement on or in a wound site. Alternatively, one or more of the porous, semipermeable and other optional components may be separate from one another and placed on or in the wound site sequentially, with the semipermeable component completely covering the wound site and porous component, which is in direct contact with the wound site. The dressing is often sized and shaped to fit on or in the wound site. In some embodiments, the dressing may be sized and shaped to extend beyond the perimeter or area of a wound or tissue site to be treated. The tissue derived porous component of the dressing may also be serially applied in layers either at the time of initial application or with subsequent applications to add volume or bulk to the treatment area as needed.

The tissue derived porous matrices described herein are suitable for use as the porous component of a wound dressing and may comprise the entire porous component or a portion thereof. Furthermore, the porous component may comprise one or more portions, sections or layers, each comprising one or more tissue derived porous matrices, where the tissue derived matrices may have been produced from the same or different types of recovered tissue.

The tissue derived porous matrices described herein are useful and beneficial for treating (i.e., placement in and near, with or without reduced or negative pressure apparatus and techniques) various types of wounds including, without limitation, chronic, acute, traumatic, subacute, dehisced wounds, partial thickness burns, ulcers, pressure ulcers, tunneling wounds, exposed fistulas and flaps. Additional types of wounds which may be beneficially treated using the tissue derived porous matrices described herein include surgical wounds such as, without limitation, donor sites, post-Moh's surgery, post-laser surgery, and podiatric (e.g., interventions, amputations), cancer or tumor removals or extirpations, and draining wounds.

As described above, the tissue derived porous matrices may be substantially acellular, which means that the majority of the endogenous cells and cellular material (i.e., greater than 50 wt % of the originally present cellular DNA material) have been removed from the recovered tissue during processing. Accordingly, in addition to providing a resorbable three dimensional scaffold for cell infiltration and new tissue ingrowth, the tissue derived porous matrices lack immunogenicity and are, therefore, highly biocompatible. In some embodiments, without limitation, greater than about 80 wt %, or greater than about 90 wt %, or greater than about 95 wt %, of the originally present cellular DNA material has been removed from the tissue derived porous matrices, which means the matrices contain less than about 20 wt %, or less than about 10 wt %, or less than about 5 wt %, of their originally present cellular DNA material.

Additionally, the methods making the tissue derived porous matrices, which will be described in detail below, typically result in the matrices retaining sufficient beneficial endogenous substances which facilitate various tissue healing and remodeling mechanisms including, without limitation, extracellular matrix production and deposition, cell infiltration and proliferation, and angiogenesis. The ability of the tissue derived porous matrices to facilitate angiogenesis and support new tissue formation when used to treat wound sites with reduced or negative pressure is believed to be a benefit previously unseen and unrealized with previously available reduced or negative pressure wound dressings. The ability of the tissue derived porous matrices to be optimized for cell infiltration and tissue regeneration via tuned pore sizes, porosity, and degradation rate is believed to be a benefit previously unseen and unrealized with previously available standard wound dressings. Furthermore, the tissue derived porous matrices may be coated with, infused with, or otherwise include exogenous cells, growth factors, extracellular matrix components, nutrients, integrins, or other substances such as, but not limited to, those which further promote cell migration, attachment, proliferation, growth and activity.

The tissue derived porous matrices may also include or be combined with one or more exogenous biocompatible materials, which may or may not also be biologically active. Such exogenous materials include, but are not limited to: polymers (natural and synthetic), ceramics, metals, other biomaterials, and combinations thereof. Combining the tissue derived porous matrices with one or more such additional biocompatible materials may be performed, for example without limitation, by one or more of mixing, blending, layering, coating, and otherwise contacting, and may form a homogeneous combination or not. Such combination with one or more exogenous materials may be performed for any of several reasons such as, without limitation, modifying handling characteristics or other properties (e.g., flowability, manual shapability, moldability, degree of shape retention or memory, cohesiveness, agglomeration, flowability, porosity, etc.), or enhancing or adding functionality (adhesion to recipient, retention in or on recipient, adding exogenous tissue-forming potential, infection prevention, pH modification, increasing mass and/or available surface area, other bioactivity, etc.).

Ceramics suitable for combination with the tissue derived porous matrices are biocompatible and include those known now and in the future such as, without limitation, aluminum oxides, calcium oxides, aluminosilicates, hydroxyapatites, tricalcium phosphates, polytetrafluro ethylene (PTFE)—carbon composites, zirconium oxides, silicon carbides, titanium nitrides, boron nitrides, carbides, and composites and combinations thereof. Metals suitable for combination with the tissue derived porous matrices are also biocompatible, and include those known now and in the future such as, without limitation, titanium, chromium, tantalum, zirconium, magnesium, stainless steel, and alloys and combinations thereof.

Suitable natural and synthetic polymers are biocompatible and include those known now and in the future. The polymers may be biodegradable and present in compositions with tissue derived porous matrices in proportions selected to provide grafts having various preferred rates of degradation and resorption of the implant and the tissue derived porous matrices. Suitable synthetic polymers include, but are not limited to, bioabsorbable polymers such as polylactic acid (PLA), polyglycolic acid (PGA), polylactic-coglycolide acid (PLGA), and other polyhydroxyacids, polycaprolactones, polycarbonates, polyamides, polyanhydrides, synthetic polyamino acids, polyortho esters, polyacetals, degradable polycyanoacrylates and degradable polyurethanes, as well as a polylactide-coglycolide (PLAGA) polymer or a polyethylene glycol-PLAGA copolymer. Examples of natural polymers include, but are not limited to, proteins such as albumin, collagen, fibrin, and polyamino acids, oligosaccharides (e.g., chitosan), and polysaccharides (e.g., alginates, hyaluronic acid and its derivatives, heparin, and other naturally occurring biodegradable polymers of sugar units). The polymeric blend may also include, without limitation, polycarbonates, polyfumarates, and capralactones.

With now reference to FIG. 1, a method for producing the tissue derived porous matrices described above will now be explained. After obtaining a sample of tissue 112 having an extracellular matrix, which may or may not involve recovering the tissue from a donor, the method for producing (manufacturing) a tissue derived porous matrix 100, requires decellularizing 118 the tissue to decrease or remove substantially all of the endogenous cells and cellular material in the tissue. The technique or method of decellularizing 118 the tissue is not particularly limited and may include any technique known now or in the future to persons of ordinary skill in the relevant art which does not completely destroy the structure of the extracellular matrix of the tissue.

Optionally and typically, but not necessarily, performed prior to decellularizing 118, the method for producing the tissue derived porous matrix 100 may further include the step of reducing the size of the tissue 112, either by mechanical or chemical techniques known now or in the future to persons of ordinary skill in the relevant art, Optionally and typically, but not necessarily, performed prior to decellularizing 118, the method for producing the tissue derived porous matrix 100 may further include the step of delipidating or demineralizing the tissue 116, using techniques known now or in the future to persons of ordinary skill in the relevant art, for decreasing the amount, or removing substantially all, of the lipids or the minerals, respectively, of the tissue. Whether delipidating or demineralizing the tissue 116 is performed will generally be determined according to the type of tissue being treated (e.g., adipose or bone, respectively) and the ultimate intended use of the tissue derived porous matrix.

Optionally and typically, but not necessarily, performed after decellularizing 118, the method for producing the tissue derived porous matrix 100 may further include the step of disinfecting (i.e., reducing the microbial load of the tissue) 120, by techniques known now or in the future to persons of ordinary skill in the relevant art, for decreasing the amount, or removing substantially all, of the microbes, bacteria, and other infectious substances from the tissue. Such techniques may be, without limitation, chemical, mechanical, exposure to radiation, etc., or any combination thereof.

Additionally, the method 100 may further comprise the step of combining the tissue with one or more solvents 122 such as, without limitation, water, saline, phosphate buffered solution or other salt solutions or biocompatible solvents known to persons of ordinary skill in the relevant art for resuspending, evenly distributing, increasing the volume of, or otherwise altering the handling and other characteristics of the resulting tissue derived porous matrix. The step of combining the tissue with one or more solvents is typically, but not necessarily, performed after decellularizing 118. Optionally and typically, but not necessarily, performed after combining the tissue with one or more solvents 122, the method 100 may further include the step of placing the tissue, or the combination of tissue and solvent (and, optionally, additional endogenous materials) in a container or mold 124. The container or mold may, but is not required to, have a desired or preselected shape which is imparted to the tissue, such as after the combined tissue and solvent are placed in the container or mold and subjected to a drying step 128 and/or a crosslinking step 130.

It is noted that, after decellularizing 118, the tissue may already have a plurality of pores. Optionally and typically, but not necessarily, performed after the decellularizing step 118, the method for producing the tissue derived porous matrix 100 may further include performing one or more pore formation steps 126. Such one or more pore formation steps 126 may be performed by any technique known now or in the future to persons of ordinary skill in the relevant art, including without limitation, those techniques described herein. The pore formation steps 126 may be performed to form (i.e., create) pores or modify existing pores in the tissue and may be performed more than once. In some embodiments, regardless of whether decellularizing 118 is performed, a porous tissue derived matrix already has a plurality of pores which are suitable for allowing fluid flow therethrough, in which case, there is no need to perform a pore forming or modifying step 126.

As will be described in further detail below, optionally and typically performed after decellularizing 118, the method for producing the tissue derived porous matrix 100 may further include the step of drying the tissue 128, by any techniques known now or in the future to persons of ordinary skill in the relevant art, for decreasing the amount, or removing substantially all of, the moisture (e.g., water) from the tissue. The method 100 will often include such a drying step 128, which is typically, but not necessarily, performed by lyophilizing as described in further detail hereinafter. As is understood by persons of ordinary skill in the relevant art, lyophilizing (also referred to as lyophilization) typically involves two phases—a freezing phase and a drying phase. The step of drying the tissue 128 may be performed while the tissue (with or without a solvent and/or additional exogenous material) is in a container or mold and may accomplish shaping the tissue into a desired shape (i.e., the shape of the container or mold). Another drying technique may, for example without limitation, comprise dehydrothermal processes, which involve application of heat under vacuum.

Optionally and typically, but not necessarily, performed after drying 128, the method for producing the tissue derived porous matrix 100 may further include the step of crosslinking or otherwise stabilizing the tissue derived porous matrix 130, using techniques known now or in the future to persons of ordinary skill in the relevant art, as will be described hereinbelow. For example, as will be recognized by persons of ordinary skill in the relevant art, other stabilizing techniques include, without limitation, heating and irradiation (e.g., exposure to gamma rays, ultraviolet energy, electron beam ("e-beam") radiation, etc.). Whether crosslinking or other stabilizing 130 is performed will generally be determined according to the type of tissue being treated and the ultimate intended use of the tissue derived porous matrix. A crosslinked or otherwise stabilized tissue derived porous matrix may, optionally, be subjected to a further drying step 132, such as without limitation by lyophilizing. Additionally, a crosslinked or otherwise stabilized tissue derived porous matrix may, optionally, be subjected to a further step of reducing the microbial load 134, for example but not necessarily after a further drying step 132. For example, without limitation, after crosslinking 130 is performed, and after further drying 132 is performed, a terminal sterilization step (i.e., another reduction of microbial load, or disinfecting step) 134 may be performed by any technique known now or in the future to persons of ordinary skill in the relevant art.

Lyophilizing may be performed to accomplish the formation of pores (e.g., step 126), to accomplish drying (i.e., step 128), to accomplish further or additional drying (e.g., step 132), or a combination of such steps 126, 128, 132. Thus, in some embodiments the step of forming pores 126 may be the same as, or performed concurrently with, the step of drying (128) by lyophilizing. Without being limited by theory, it is believed that performing lyophilizing within certain parameters forms pores in a consistent and controllable manner, as will now be described.

For example, prior to lyophilizing, the step of combining the tissue with a solvent (122) may include adding (combining) water (or another aqueous solvent) with the tissue to form a tissue and water mixture having a ratio of tissue to water of from about 1:99 to about 99:1, based on 100 parts of total tissue and water mixture. This "excess" water facilitates formation of water crystals in the tissue during the freezing phase of lyophilizing, which are then removed during the drying phase of lyophilizing, leaving pores (i.e., vacant spaces) in the lyophilized tissue. In some embodiments when lyophilizing is performed to form pores in the tissue being processed to make a biosponge, the ratio of tissue to water may generally be from about 1:99 to about 60:40, or any ratio or value therebetween, such as from about 1:99 to 50:50, or from about 1:99 to 40:60, or from about 5:95 to about 60:40, or from about 10:90 to about 60:40, or from about 10:90 to about 50:50.

The amount of water combined with the tissue (i.e., the ratio of tissue to water) prior to lyophilizing may vary according to the type of tissue used to make the tissue derived porous matrices (biosponges), as is determinable by persons of ordinary skill. For example without limitation, when the tissue type used is placental, the ratio of tissue to water may be as low as about 1:99. For example without limitation, when the tissue type used is dermis, the ratio of tissue to water may be from about 1:99 to about 40:60, or any ratio or value therebetween, such as from about 10:90 to about 40:60, or from about 10:90 to about 30:70, or from about 15:85 to about 30:70.

In some embodiments when lyophilizing is performed to form pores in the tissue being processed to make a biosponge, the rate of freezing during lyophilizing (i.e., during the freezing phase thereof) should typically be in a range from about 0.1° C./minute to about 2° C./minute or any range or value therebetween. For example without limitation, the rate of freezing during lyophilizing, may be from about 0.1° C./minute to about 2° C./minute, such as from about 0.1° C./minute to about 1° C./minute, or from about 0.0.2° C./minute to about 0.5° C./minute, from about 0.3° C./minute to about 0.4° C./minute.

In some embodiments when lyophilizing is performed to form pores in the tissue being processed to make a biosponge, the drying time for the drying phase of lyophilizing should typically be in a range of from about 720 minutes (0.5 days) to about 10,080 minutes (7 days), or any range or value therebetween, such as from about 1440 minutes (1 day) to about 10,080 minutes (7 days), or from about 4320 minutes (3 days) to about 8640 minutes (6 days), from about 7200 minutes (5 days) to about 8640 minutes (6 days). As is understood by persons of ordinary skill in the relevant art, the drying time may be even more than 7 days depending on the dimensions of the biosponge to be dried.

Figure 2:
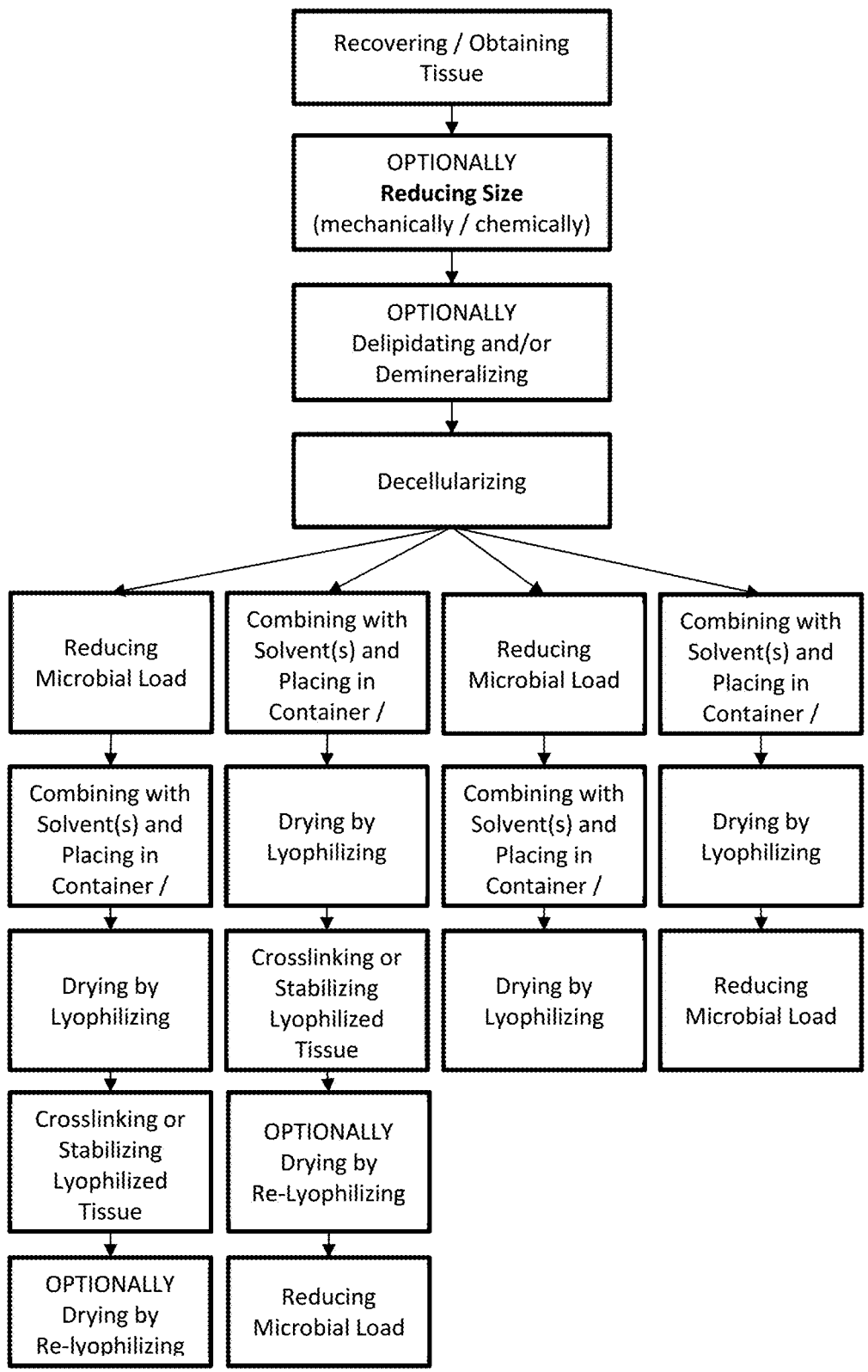
FIG. 2 is a flowchart showing several possible alternative exemplary embodiments of the method for producing tissue derived porous matrices.

FIG. 2 provides several possible alternative embodiments of the method for producing the tissue derived porous matrices 200 employing several of the above-described steps in various orders. All of these embodiments 200, as well as others, which will be apparent to persons of ordinary skill in the relevant art, are within the scope of the present disclosure for performing the method for producing the tissue derived porous matrices.

The method for producing the tissue derived porous matrices 100 may further include one or more packaging steps (not shown). The method 100 may also include one or more combining or formulating steps (not shown) whereby the tissue derived porous matrices are mixed, attached or otherwise combined with other materials including, without limitation, cells, growth factors, other substances (e.g., antibiotic, antimicrobial, pharmaceutically effective compounds, excipients, carriers, etc.), other types of synthetic or naturally derived matrices (e.g., an adipose derived porous matrix combined with a bone derived matrix or a synthetic dissolvable, resorbable matrix, etc.), and other types of materials (e.g., a resorbable monolithic or mesh scaffold, etc.).

As is understood by persons of ordinary skill in the relevant art, a carrier may be biologically inert or inactive. A carrier may be biologically active, for example, in a manner which enhances the tissue-forming potential of the tissue derived porous matrices, or the carrier may provide or induce another biological activity, property or effect which may be unrelated, complementary or supplemental to the tissue-forming potential of the tissue derived porous matrices.

Suitable biocompatible carriers may be naturally occurring or derived therefrom, or synthetic, or a combination of such materials. Generally, suitable biocompatible carriers include for example, without limitation, buffered solutions, glycerol, hyaluronate, polyethylene glycol, stearates, cellulose-derived materials (e.g., chitosan, alginates, hydroxypropyl cellulose (HPC), carboxymethyl cellulose (CMC), hydroxypropyl methyl cellulose (HPMC), etc.), and combinations thereof. Particularly suitable biocompatible carriers for use with the tissue derived porous matrices include, without limitation, hyaluronate, glycerol and buffered solutions. In some embodiments, the biocompatible carrier comprises sodium hyaluronate. In some embodiments, the biocompatible carrier comprises sodium hyaluronate and a buffered saline solution. In some embodiments, the biocompatible carrier comprises glycerol.

In some embodiments, the carrier includes at least one of an isotonic solution, a sodium chloride solution, lactated Ringer's solution, a phosphate-buffered saline solution (PBS), platelet rich plasma (PRP), bone marrow aspirate (BMA), and hyaluronic acid (HA) or a derivative thereof such as sodium hyaluronate. In embodiments, the carrier is a sodium chloride solution at a concentration of about 0.10% to about 1%. In some such embodiments, the sodium chloride solution is at a concentration of about 0.9%. In some embodiments, the carrier is a mixture of sodium hydaluronate and an aqueous solution. In some embodiments, the sodium hyaluronate has a molecular weight of from about $5.0 \times 10^3$ to about $3.0 \times 10^6$ Daltons, such as from about $6.0 \times 10^5$ to about $3.0 \times 10^6$ Daltons and is mixed with an aqueous solution to form a matrix-carrier mixture having a viscosity ranging from about 1000 centipoise to about 275,000 centipoise, such as from about 6,000 to about 275,000 centipoise. In some embodiments, the aqueous solution of the carrier comprising sodium hyaluronate is, for example without limitation, one or more of water, saline, phosphate buffered solution (PBS), isotonic saline, and the like.

In some embodiments, the carrier comprises thrombin. In some embodiments, the carrier comprises fibrin. In some embodiments, the carrier comprises glycerin. In some embodiments, the carrier comprises gelatin. In some embodiments, the carrier comprises collagen. In some embodiments, the carrier comprises lecithin. In some embodiments, the carrier comprises a sugar. In some embodiments, the sugar comprises a polysaccharide. In some embodiments the carrier includes a combination of two or more carrier components.

As will be understood and practicable by persons of ordinary skill in the relevant art, where one or more steps of the method 100 are described herein as being performed "prior to" or "after" another step of the method 100, such one or more steps may, but need not, be performed immediately prior to or after said another step, such that other steps may be performed in between such one or more steps and said another step. Additionally, while the method 100, 200 should include at least the steps of obtaining a sample of tissue 112 and decellularizing the tissue 118, each of the "optional" steps described above may be performed, or may be omitted from a particular embodiment. The method for producing the tissue derived porous matrices 100, 200, in addition to the aforesaid obtaining and decellularizing steps 112, 118, may include any combination of the above-described optional steps 114, 116, 120, 122, 124, 126, 128, 130, 132, 134 and any one or more of the treatment steps 114, 116, 118, 120, 122, 124, 126, 128, 130, 132, 134 may be performed in any order and may be performed more than once.

Tissues recovered from donors (i.e., "recovered tissues") are processed using a combination of physical and chemical methods to produce a tissue derived porous matrix of defined dimensions, porosity, mechanical properties, and controlled resorption rate. The method further includes process steps for decellularization and, optionally, reducing microbial/viral load. In some embodiments, the method may further include partial or complete drying, or dehydration, to provide a final "dry" product. More particularly, a final "dry" tissue derived porous matrix contains less than about 20 wt % of water/moisture, based on the total weight of the tissue derived porous matrix, such as less than about 15 wt %, or less than about 10 wt %, or less than about 8 wt %, or less than about 6 wt %, or less than about 5 wt % water/moisture. In some embodiments, the method does not include drying/dehydration and the tissue derived porous matrices remain hydrated, through packaging, storage and use, so that they need not be rehydrated at the time of use. Partially dry or undried tissue derived porous matrices contain greater than about 20 wt % of water/moisture, based on the total weight of the tissue derived porous matrix, such as greater than about 25 wt %, or greater than about 30 wt %, or greater than about 35 wt %, The tissue derived porous matrices may be crosslinked and, in some embodiments, such crosslinked matrices contain more than about 20 wt % of water/moisture, based on the total weight of the tissue derived porous matrix. The crosslinked tissue derived porous matrices may, in other embodiments, be provided as a final "dry" product that contains less than about 20 wt % of water/moisture, based on the total weight of the tissue derived porous matrix, such as less than about 15 wt %, or less than about 10 wt %, or less than about 8 wt %, or less than about 6 wt %, or less than about 5 wt % water/moisture.

Without wishing to be limited, it is believed that tissue derived porous matrices having a compression force deflection (CFD) in a range of from about 2 kiloPascals (kPa) to about 20 kPa, when a moisture saturated tissue derived porous matrix is compressed to at least 50% of its original uncompressed thickness, would be most familiar and useful to practitioners (e.g., physicians, surgeons, nurses, medical assistants, etc.). For example, where the recovered tissue used to prepare the porous matrices is dermis, a CFD of from about 2 to about 10 kPa would typically be acceptable, but where the recovered tissue is placental tissue, a CFD of up to about 20 kPa would likely be acceptable.

To maximize some of the above-stated benefits when used to enhance wound healing, when positioned in a wound site and subjected to reduced pressure in a range of from about −50 mm Hg to about −200 mm Hg, it is believed that the tissue derived porous matrices should maintain at least 25% of their original mass and porous structure for a minimum of about 96 hours.

The material of the biosponge can be derived from chemically solubilized, mechanically reduced or intact extracellular matrix (ECM) obtained from decellularized tissue of the types including, but not limited to, adipose, dermis, placental tissue, fascia, bone, cartilage, muscle or composite of adipose/fascia or adipose/dermis/fascia, or from xenogeneic sources. Decellularization can be achieved using, without limitation, one or a combination of the following techniques: highly acidic solutions, highly basic solutions, hypertonic solutions, hypotonic solutions, alcohols, detergents, and physical methods such as pressure and cyclic freeze-thaw.

Such material may also be subjected to a microbial/viral load reduction (e.g., sterilization) step which can be achieved using, without limitation, one or a combination of the following techniques: chemical sterilants, contact with ethylene oxide, gamma irradiation, electron beam irradiation, contact with supercritical carbon dioxide, exposure to heat, contact with highly acidic solutions, or contact with highly basic solutions. For example, without limitation, one or more sterilization steps, which may be performed before or after any of the method steps described herein, but which are expected to be most effective when performed after as many such steps as is practical, such as without limitation, after all other processing steps have been completed. In some embodiments, no chemical sterilants are used, but rather only by application of one or more of electron beam, gamma radiation, or heat, to the tissue derived porous matrices. In some embodiments, both chemical sterilants and other techniques are applied.

The method for making the tissue derived porous matrices may, optionally, also comprise the step of forming a plurality of pores (i.e., a porous structure), or modifying a plurality of existing pores, in the matrices by one or a combination of pore forming techniques known now or in the future. For example, without limitation, pores may be formed or modified in the tissue derived porous matrices by one or a combination of the following techniques: freezing (controlled or uncontrolled rate); freeze-drying (i.e., lyophilizing) in an open mold or around a removable lattice-like structure, with or without mixing at various ratios with an aqueous solution; porogen leaching; gas foaming; 3D printing; electrospraying; and air drying around a removable lattice-like structure.

In some embodiments, cross-linking may be performed on the matrices to maintain the stability of the biosponge and to control the resorption rate of the biosponge once applied to the wound site, by means known to those in the field, including but not limited to heat crosslinking, solution or vapor crosslinking methods with various crosslinkers mentioned below, dehydrothermal (heat treatment under vacuum) crosslinking, various photo-crosslinking methods including ultra violet (UV) irradiation, electron beam irradiation, gamma irradiation with or without riboflavin or ascorbic acid, exposure to glutaraldehyde (GA), exposure to 1-ethyl-3-[3-dimethylaminopropyl] carbodiimide (EDC) with or without N-hydroxysulfosuccinimide (NHS) in the presence or not of the amino acid lysine, exposure to genipin or other naturally derived crosslinkers, exposure to Grape seed extract mainly composed of proanthocyanidin (PA), exposure to acyl azide such as hydrazine or diphenylphosphorylazide (DPPA), exposure to hexamethylene diisocyanate (HMDIC).

In some embodiments, the cross-linking is not uniform and the porous structure may be crosslinked so as to obtain a gradient of crosslinking degrees throughout the structure cross-section, which produces varying degrees of stability and resorption of the collagen.

In one embodiment, the biosponge is composed of two or more layers of ECM sponges of varying porous degrees that have been chemically/physically bound.

In some embodiments, the biosponge may also have macro-pores which are transverse channels of from about 0.5 to about 2.0 millimeters (mm) in diameter, such as without limitation, from about 0.5 to about 1.5 mm and evenly dispersed throughout the surface of the sponge, that can be introduced before or after crosslinking.

EXAMPLES

The following descriptions, flowcharts and tables provide exemplary embodiments of methods for making the tissue derived porous matrices from particular recovered tissue types, including human placenta and human dermis.

Test Methods for Characterization

The following descriptions provide explanations for each of the test methods employed to produce the characterization data and information provided below in the Biosponge Testing Matrix tables for each embodiment (i.e., placental and dermal).

Compressive Deflection Force Testing (Based on ASTM D3574)
1. Measure the height of the sponge.
2. Measure the length and width, or diameter of the sponge.
3. Slowly add Simulated Chronic Wound Fluid (sCWF) [50% TrisHCl titrated to pH 8-8.5+50% FBS, 2% w/v peptone+40 mg/L elastase], until the sponge is completely wet and saturated, when excess fluid begins to seep out of sponge.
4. Place the saturated sponge onto the testing stage.
5. Calculate 50% of the height of the sponge based on previous measurements.
6. Using a force gauge with a flat test plate, move the plate downward until the clearance between the testing stage and the test plate is equal to the calculated 50% height, compressing the sponge to 50% of its original height.
7. Note the peak force (in N) recorded by the force gauge during the test.
8. Divide the peak force by the surface area of the sponge's top face, then convert from units of $N/mm^2$ to units of kPa per known conversion values.

Unconfined Compression Testing
1. Samples were cut to a uniform size of 1.5×1.5×2 cm.
2. Samples were rehydrated in PBS for 1 minute.
3. A compression ramp test to 60% strain (12 mm) was performed at a strain rate of 0.1 mm/sec on a test frame (ElectroForce 5500, TA Instruments)
4. Material stress ($\sigma$) was calculated as load divided by cross-sectional area.
5. Material strain ($\varepsilon$) was calculated as change in height divided by initial height.
6. The elastic compressive modulus (E) was calculated from the slope of the upper region of the stress-strain curve.
7. The resilience was calculated as the area under the stress-strain curve through 60% strain.

Compressive Stress-Relaxation Testing
1. Samples were cut to a uniform size of 1.5×1.5×2 cm.
2. Samples were rehydrated in PBS for 1 minute.
3. To simulate the load applied during use with common negative pressure devices, the common setting of 125 mmHg was converted to a load of 3.6N given the sample geometry.
4. Using the data from the unconfined compression testing the 3.6N was converted to a strain ($\varepsilon'$) to be applied to each sample.
5. Using the test frame, a displacement ramp was applied to the sample at 4 mm/sec until $\varepsilon'$.
6. The sample was held at this strain for 180 s before unloading at a rate of 4 mm/sec.
7. The sample was allowed some time to fully relax unloaded before applying the strain ramp and release in steps 5 and 6 for another iteration.
8. The resulting data was used to model the time-dependent behavior of the sample according to the equation $\sigma(t)=Ae^{-t/\tau}+B$ and fitting the coefficients and time constant ($\tau$) to the experimental data.

Rheological Testing
1. Samples were cut to a uniform size of 1.5×1.5×2 cm.
2. Samples were rehydrated in PBS or BSA for 1 minute.
3. The shear properties of the samples were measured using a rheometer (Anton Paar MCR 301).
4. A 25 mm diameter parallel plate geometry was used to apply shear at a measurement height of 8.5 mm.
5. An oscillatory amplitude sweep was performed on each sample at a constant angular frequency (0.10% to 100% strain at 1 rad/s and 10 rad/s) to measure shear stress ($\sigma$) as a function of strain ($\varepsilon$).
6. Shear modulus (G) was calculated using this data and the equation $\sigma=G\times\varepsilon$.

Degradation Testing
1. 1.5×1.5×2 cm samples were rehydrated in PBS or PBS with BSA at a concentration of 1 g/dL albumin (common concentration in wound exudate found in literature).
2. Each samples was placed in a separate 50 mL conical tube and 15 mL of solution was added to each.
3. The samples were stored in a static incubator at 37° C. for 7 or 14 days.
4. The samples were tested for unconfined compression and rheology as detailed above.

Fluid Flow Testing
1. Samples were cut to 28 mm diameter to fight tightly into a 60 mL syringe with a 26.72 mm inner diameter.
2. The samples were coated on the edges with super glue and each positioned at the base of a syringe.
3. The syringes were places in a syringe pump with tubing leading to a 3-way stopcock split between a Dwyer pressure gauge and a beaker with PBS.
4. The syringe pump was used to set flow rates to withdraw fluid through the sample.
5. Flow rates of 30, 40, 50, 60, 70 mL/min were set and the pressure was recorded at each rate once stabilized.
6. The sample resistance was calculated as the slope of the best fit line of this pressure and flow data (resistance=change in pressure/change in flow).

Hydration Testing
1. Samples were cut to a uniform size of 1.5×1.5×2 cm.
2. Dry mass was recorded for each samples ($M_d$)
3. Samples were hydrated by being placed into individual 50 mL conical tubes with 15 mL of PBS and kept at 37° C. for 24 hours.
4. Samples were removed from the conical tubes and hydrated masses were recorded ($M_w$).
5. Hydration ratio was calculated as mass change percentage=$(M_w-M_d)/M_d \times 100$.

Figure 3:
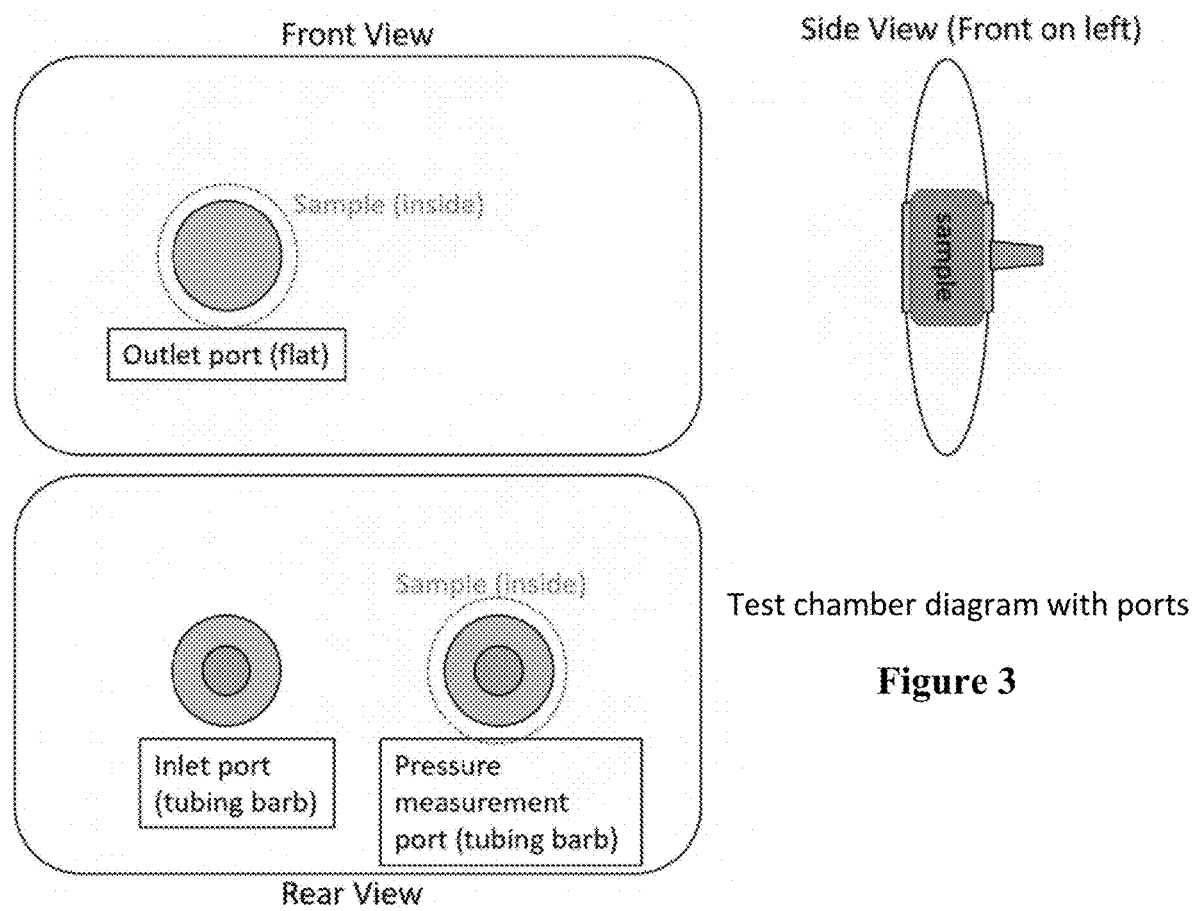
FIG. 3 is a schematic diagram of the test chamber apparatus used to assess fluid flow-through of tissue derived porous matrices described herein.
Figure 4:
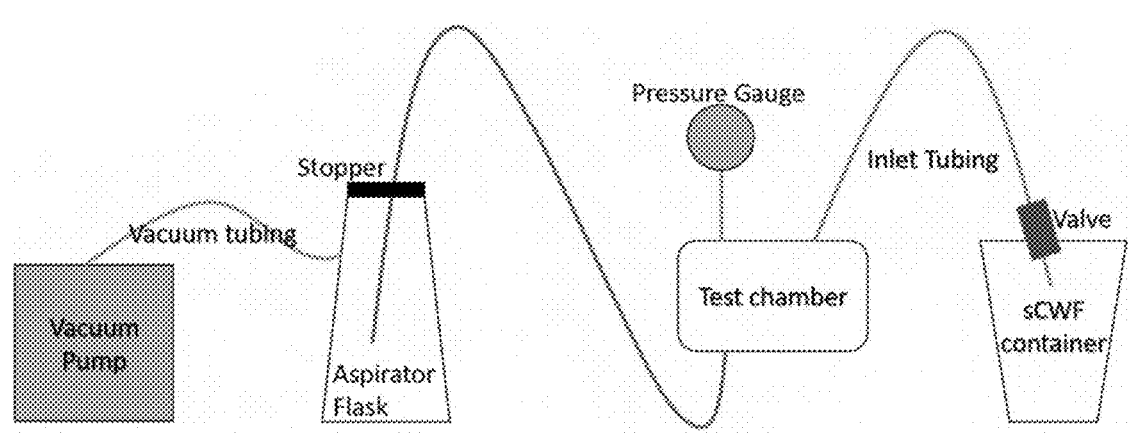
FIG. 4 is a schematic diagram of a Negative Pressure Wound Treatment (NPTW) System, including the test chamber of FIG. 3, which was used to assess fluid flow-through of tissue derived porous matrices described herein.

Fluid Flow-Through Testing (Simulated NPWT System)
1. Simulated NPWT System setup:
   a. Prepare sCWF, optionally without elastase as the test is of a short duration.
   b. Prepare a test chamber comprising a resealable pouch with ports for inlet/outlet/pressure measurement (see FIG. 3).
   c. Connect a vacuum pump to the side port of an aspirator flask. Connect a suction pad/tubing to the top port of an aspirator flask with a stopper to seal (See FIG. 4).
   d. Place the suction pad onto the outlet port and seal with drape.
   e. Connect a vacuum gauge to the pressure measurement port.
   f. Connect tubing with a valve to the inlet port.
   g. Turn on the pump and adjust vacuum to desired level (−50 mmHg gauge pressure) using the pump gauge, ensure no leaks are in the system, then turn off.
   h. Open the test chamber and place a pre-wetted test sponge between the outlet and measurement ports.
   i. Reseal the test chamber.

2. Turn on the vacuum with the inlet valve closed and allow the pouch to completely collapse under vacuum.
3. Place inlet tubing into a container containing 200 mL of sCWF, then open the inlet valve.
   a. If sCWF is not flowing into the inlet tubing, adjust vacuum level on pump until liquid begins to flow.
4. Record the time needed to pull 200 mL of sCWF through the simulated NPWT system.
   a. Using the 200 mL volume and time, calculate an average volume/min flow rate
5. Optionally, after fluid has been pulled through the system, measure the amount of sCWF collected in the aspirator flask.

Delivery of Reduced or Negative Pressure (Simulated NPWT System)
1. During Fluid Flow-through testing with sponge inserted but inlet still closed, record the vacuum measured by the gauge.
2. During Fluid Flow-through testing with sponge inserted and inlet opened, record the vacuum measured by the gauge.

Durability—Qualitative (Cutting)
1. Cut a dry sponge using surgical scissors and observe any breakage or cracking
2. Cut a wetted sponge using surgical scissors and observe any breakage or cracking.

Durability—Qualitative (High Vacuum)
1. After Fluid flow-through testing is completed, increase vacuum level on the pump to −200 mmHg and allow to pull more sCWF through the line.
2. After 1 minute, turn off the pump and remove the sponge.
3. Visually inspect the collected fluid in the aspirator flask for presence of tissue particulates.
4. Visually inspect the sponge for breakage or cracking.

Resorption—Simulated Chronic Wound Fluid Enzyme Degradation
1. Place sponges saturated with sCWF into small sealable containers to simulate sponges being exposed to chronic wound fluid enzyme degradation.
2. For worst case, add additional sCWF and completely immerse sponge.
3. Seal containers and place into a water bath set to 37° C.
4. Keep saturated and/or immersed sponges in the water bath for 5 days.
5. Remove containers from the water bath.
6. Open the containers and remove the sponges.
7. Visually inspect the fluid remaining in the container for presence of tissue particulates.
8. Test the saturated and/or immersed sponges per Fluid Flow Through test method.

Pore Size—Scanning Electron Microscopy (SEM)
1. Cut samples from a sponge to generate vertical and horizontal cross-sections.
2. Place double-sided carbon tape onto SEM specimen pin stubs.
3. Place each sample onto the expose carbon tape of a stub and allow the sample to come into full adhesive contact.
4. Use a sputter coater [Leica EM ACE600 Sputter Coater] to coat each sample with approximately 5 nm of iridium deposition, optionally with sputtering sequences including 0-45° tilt to ensure full specimen coverage.
5. Image the specimens using a scanning electron microscope [XL30 FEG-SEM].

6. Analyze using ImageJ software:
   a. Set Scale
   b. Apply Auto Threshold
   c. Measure Particles (500 $um^2$ or larger)
   d. Summarize (Feret Mean)

Porosity (Liquid Displacement)
1. Add 50 mL absolute ethanol ($V_1$) into a wide mouth 100 mL graduated cylinder, ensuring the cylinder is wide enough to accommodate sponge samples.
2. Place a foam test sample into the graduated cylinder such that it is submerged in the ethanol.
3. Pull a vacuum in the graduated cylinder to draw out air bubbles in the sponge and ensure complete wetting of internal pores.
4. Measure the volume of the ethanol with the sample submerged ($V_2$).
5. Remove the sponge sample carefully, without compressing the sample to avoid expelling liquid from the sample.
6. Measure the remaining volume of ethanol in the graduated cylinder ($V_3$).
7. Calculate porosity of the sample by the formula ($V_1$-$V_3$)/($V_2$-$V_3$).

Matrix Composition—Biological Factors
1. Cut samples from a sponge.
2. Send sponge sample to third party histology lab for embedding, section, and then histological or immunohistochemical (IHC) staining:
   a. H&E staining
   b. Glycosaminoglycans (GAGs) via Safranin O staining
   c. Collagen III via IHC
   d. Collagen IV via IHC
   e. Hyaluronic Acid (HA) via IHC
   f. PDGF-bb via IHC
   g. VEGF via IHC
3. Visually evaluate slides for presence of positive staining as compared to positive and negative control slides.

Residual Moisture Content Determined Per USP<731> Loss on Drying
1. 1-2 grams of sponge was sent for analysis.
2. Oven is preheated to 105° C.±2 C.
3. Place sample dish in oven for 30 minutes, place in dessicator to cool.
4. Place dish on balance and weigh. Tare balance.
5. Place sample in dish and weigh.
6. Place dish with sample into heated oven for 24 hours.
7. After 24 hours, place dishes in dessicator to cool.
8. Place on balance and weigh.
9. Percent residual moisture (%) is calculated as (Initial weight-Dry sample weight)/Initial weight×100.

Pre-Clinical Efficacy in an Animal Model

A pre-clinical study intended to evaluate the efficacy of the biosponge in an animal model will be performed and is described below, followed by listings of study evaluation parameters and scales. The study will be conducted in a porcine model to assess wound bed granulation and tissue incorporation of the biosponge into the wound bed. Healing will be compared to currently available synthetic foam for NPWT as a control. It is expected that the results of this study will show faster and/or more thorough granulation tissue formation in the biosponge test group versus the synthetic foam control.

Protocol Design Overview:
One (1) pig will be used in this study which will run for a total of seven (7) days.
Experimental procedure
Sixteen (16), full-thickness, 3 cm×3 cm square wounds will be created freehand on each pig using a scalpel blade and forceps; eight (8) on each side of the pig
Wounds will NOT be infected in this study (possible perioperative antibiotic use)
Wound Dressings:
Row A: Control—Synthetic NPWT foam dressing (KCl GranuFoam)
Foam material and drape/suction pad will be replaced at each dressing change
Row B: Treatment 1—Biosponge Formulation #1
drape/suction pad only will be replaced at each dressing change
Row C: Treatment 2—Biosponge Formulation #2
drape/suction pad only will be replaced at each dressing change
Row D: Treatment 3—Currently available meshed acellular dermal matrix in conjunction with synthetic NPWT foam dressing
drape/suction pad only will be replaced at each dressing change
N=4 data points per dressing application
Appropriate ports will be applied over the foam dressings and a commercially available NPWT device will be connected.
The device will be turned on and ran on the −125 mmHg continuous setting throughout the study.
Pig will be sacrificed on Day 7
Assessment parameters include:
Digital caliper measurements for wound size and depth: D0, D2, D4, and D7
Digital photographs will be taken on: D0, D2, D4, and D7
Histology
Each wound will be excised with 1cm surrounding normal tissue circumferentially and deep to the wound and fixed in 10% neutral buffered formalin.
Samples will be sent to a histopathology laboratory for trimming, embedding, sectioning, staining, and histopathology/histomorphometry evaluation.
Histopathology:
H&E:
Adverse tissue reaction scoring (rubric below)
Collagen maturation scoring (semi-quantitative per rubric)
Histomorphometry:
H&E:
Granulation tissue thickness (measured at 3 evenly spaced intervals across wound bed)
Granulation tissue ingrowth into dressing material (if applicable)
CD31:
Vascular density quantification within Region of interest (ROI)
Typical Histopathology Evaluation Parameters:

| | |
|---|---|
| Overall inflammation (wound bed) | 0 = Absent |
| Overall inflammation (surrounding residual test article or control article material), when applicable | 1 = Minimal |
| | 2 = Mild |
| Edema/seroma formation | 3 = Moderate |
| Serocellular debris at the wound surface | 4 = Marked/Severe |
| Hemorrhage | |
| Necrosis within wound bed | |
| Abscess formation (superficial wound bed) | |
| Granuloma formation | |
| Microgranuloma formation | |
| Mineralization | |
| Inflammatory Response: | 0 = Absent |
| Neutrophils | 1 = Rare, 1-5/hpf (MNGC = 1-2/hpf) |
| Eosinophils | 2 = 6-10/hpf (MNGC = 3-5/hpf) |
| Lymphocytes | 3 = Moderate, heavy infiltrates |
| Plasma Cells | 4 = Packed (MNGC = sheets) |
| Macrophages | (/hpf = per high-powered (400x) field) |
| Multinucleated Giant Cells (MNGC) | |
| Nature of newly deposited collagen: | 0 = No collagen deposition. |
| Collagen maturation of superficial wound bed | 1 = Scanty collagen deposition as a loose, poorly organized stroma. |
| Collagen maturation of deep wound bed | 2 = More notable collagen deposition than Score 1, with the majority of the stroma still loose and poorly organized with collagen fibers predominately oriented parallel and perpendicular to the skin surface. |
| | 3 = More notable collagen maturation than Score 2, with the majority of the stroma appearing dense and organized with collagen fibers oriented parallel to the skin surface. |
| | 4 = More notable collagen maturation than Score 3, with majority of stroma having the appearance of native dermal collagen. |
| Epithelialization at the wound edges | 0 = No ingrowth of epithelium beyond wound edge. |
| | 1 = Less than 1 mm of ingrowth of epithelium beyond wound edge on one or both sides of the wound. |
| | 2 = Greater than 1 mm of ingrowth of epithelium beyond wound edges on both sides of the wound but not fully re-epithelialized. |
| | 3 = Surface of wound completely covered by epithelium. |

| | |
|---|---|
| Granulation tissue filling of wound bed | 0 = No granulation tissue filling of wound bed.<br>1 = ~1%-25% of wound bed filled.<br>2 = ~26%-50% of wound bed filled.<br>3 = ~51%-75% of wound bed filled.<br>4 = ~76%-100% of wound bed filled.<br>5 = >100% of wound bed filled (excessive granulation tissue). |
| Vascularization within wound bed | 0 = Absent.<br>1 = Very few small vessels scattered throughout the wound bed.<br>2 = Numerous blood vessels in few areas with mostly low numbers of blood vessels throughout the wound bed.<br>3 = Moderate, numerous blood vessels interspersed throughout portions of the wound bed with areas of lower vascular density interspersed throughout.<br>4 = Marked, numerous blood vessels interspersed throughout the wound bed. |
| Other Findings:<br>Foreign debrisBacteria<br>Fibrous Capsule | P = Present<br>A = Absent<br>When present, the fibrous capsule will be measured in three random locations per slide using an ocular micrometer. |

Example 1: Placenta Biosponge Prepared from Recovered Human Placenta Tissue

Figure 5:
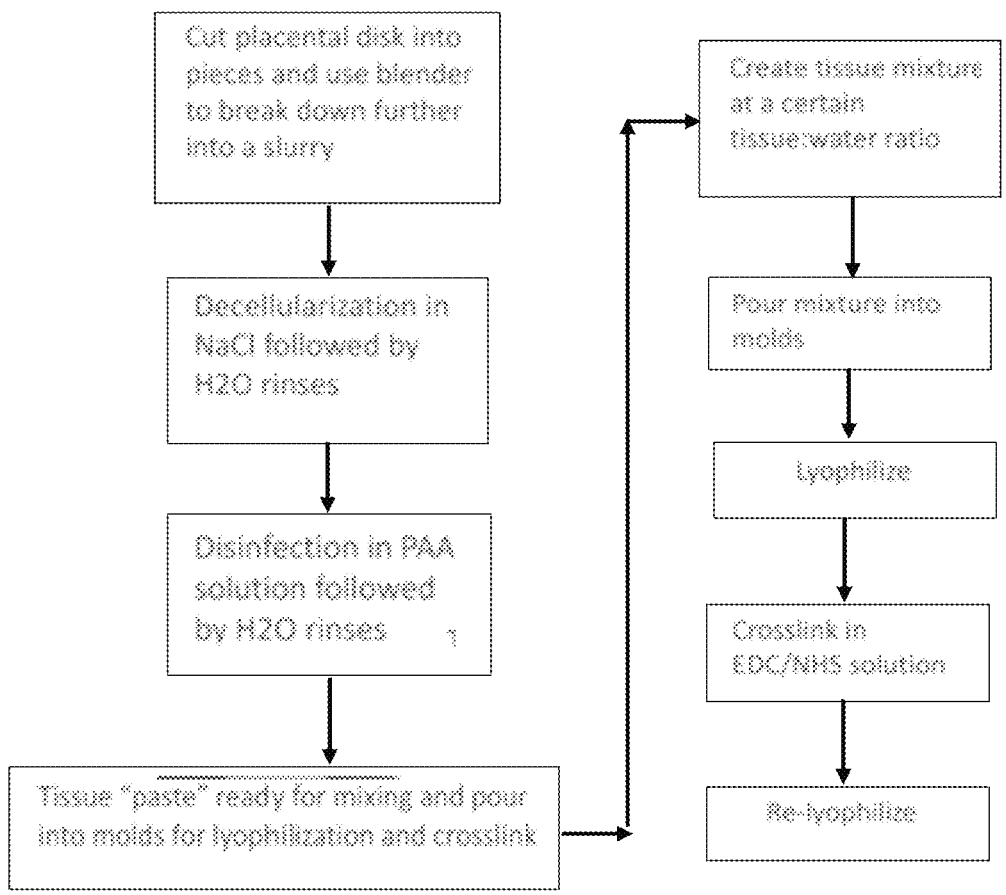
FIG. 5 is a flowchart showing the basic steps of an exemplary method for producing tissue derived porous matrices comprising placenta tissue (a placenta biosponge) in accordance with the present invention.

A placenta biosponge was prepared from human placenta tissue according to the general method shown in FIG. 5, with the specific parameters performed described below.

Initial Processing, Up Through Decellularization:

A placenta disk and optionally also the umbilical cord and amnion/chorion membranes, were first cleaned in water. The tissue was then subdivided and blended with a hypertonic solution to create a tissue/hypertonic solution mixture. The mixture was agitated to decellularize the tissue components. The mixture was then centrifuged and then resuspended and agitated in water to remove the hypertonic solution.

1. A placenta was obtained, comprising the disk, the umbilical cord and membranes in addition.
2. The tissue was soaked and massaged in room temperature water to help expel excess blood and remove blood clots.
3. The tissue was then cut into smaller pieces using a scalpel.
4. Avoiding transfer of excess liquid, the tissue pieces were combined with 1 L 1M NaCl solution in a heavy duty blender [Waring].
5. The tissue mixture was blended for approximately 1 minute on High speed, two times.
6. The tissue mixture was then transferred into a 2 L flask and agitated on an orbital shaker at 90 to 150 rpm for approximately 2 hours.
7. The tissue mixture was transferred into centrifuge bottles and centrifuged at 4600 RPM for 10 minutes, then the supernatant was poured off.
8. A total of 1 L of water was combined with the remaining tissue pellets and transferred into a 2 L flask and agitated on an orbital shaker at 90 rpm for approximately 5 minutes.
9. The tissue mixture was transferred into centrifuge bottles and centrifuged at 4600 RPM for 5 minutes, then the supernatant was poured off.
10. A total of 1 L of water was combined with the remaining tissue pellets and transferred into a 2 L flask and agitated on an orbital shaker at 90 rpm for approximately 5 minutes.
11. The tissue mixture was transferred into centrifuge bottles and centrifuged [at 4600 RPM for 10 minutes], then the supernatant poured off.
12. The tissue pellets were recovered and frozen at −20 C for staging prior to disinfection.

Disinfection (i.e., Reducing Microbial Load):

The decellularized tissue was blended with a peracetic acid-based disinfection solution and then agitated to disinfect the tissue. The tissue mixture was subjected to a series of centrifugation steps, each followed by agitation in water, to remove the disinfection solution. The remaining tissue was combined with water in a variety of potential ratios to create a tissue mixture, which was then frozen prior to lyophilization.

1. The tissue was combined with 1 L of peracetic acid based disinfection solution in a heavy duty blender (Waring).
2. The tissue mixture was blended for approximately 1 minute on High speed.
3. The tissue mixture was then transferred into a 2 L flask and agitated on an orbital shaker at 90 rpm for approximately 2 hours.
4. The tissue mixture was transferred into centrifuge bottles and centrifuged at 4600 RPM for 10 minutes, then the supernatant poured off for disposal.
5. A total of 1 L of water was combined with the remaining tissue pellets in a heavy duty blender and blended for approximately 1 minute on High speed.
6. Tissue was subjected to multiple (8) rinses with agitation sufficient to remove PAA residuals. Tissue was subjected to a 1-minute blending step on High after the 7$^{th}$ rinse, and before the final rinse.
7. The tissue mixture was transferred into centrifuge bottles and centrifuged at 4600 RPM for 10 minutes, then the supernatant poured off.
8. The tissue pellets were recovered and stirred to make a more homogenous mixture, and then weighed in a tared container. This was considered the baseline "$_{100}$% tissue mixture".
9. Water was combined with the tissue mixture to obtain a 50% tissue mixture.
10. The final tissue mixture was then aliquotted into suitable containers for lyophilization, consisting of 2 6-well plates and a small aluminum cup.

Drying/Lyophilization:

The tissue mixture was dried by lyophilizing: tissue was placed into a lyophilizer and the lyophilization cycle provided in the chart below was run to obtain a dried tissue form.

Lyophilization Cycle—Placental Biosponge Recipe

| Recipe Phase | Temperature (° C.) | Time (min) | Vacuum (mTorr) | Ramp/Hold |
|---|---|---|---|---|
| Thermal Treatment | | | | |
| Step 1 | −40 | 240 | | Hold |
| Freeze Temperature | −40 | | | Hold |
| Additional Freeze Time | | 30 | | |
| Condenser Set Point | −40 | | | |
| Vacuum Set Point | | | 600 | |
| Drying Phase | | | | |
| Step 1 | −5 | 5,760 | 600 | Hold |
| Secondary Drying Phase | | | | |
| Post Heat Step | 24 | 720 | 600 | Hold |

Crosslinking:

A chemical crosslinking solution was prepared (for example, see below). The solution was added to the dried tissue form and allowed to crosslink the tissue. After crosslinking, the solution was removed and the tissue was rinsed in water to remove residual crosslinking solution.

1. Preparation of crosslinking solution.
   a. 60 mM 1-ethyl-3-(3-dimethylaminopropyl)carbodiimide (aka EDC) and 24 mM n-hydroxysuccinimide (aka NHS) in water.
2. The crosslinking solution was slowly added to the contained lyophilized tissue, avoiding dispensing directly onto the tissue, until tissue was completely immersed. Wetting of the tissue by the solution was ensured, while avoiding pressing down to avoid collapsing the yet-uncrosslinked structure.
3. Crosslinking was allowed for 60 minutes at room temperature.
4. Excess crosslinking solution was removed and tissue was transferred into a container with an excess of water, and rinsed for 15 minutes. This was repeated for a total of 4 water rinses.
5. The rinsed tissue retained its shape and its ability to absorb liquid, as a sponge.

Final Drying/Lyophilization Step (Optional Step):

The crosslinked sponges were lyophilized again to yield dry sponges suitable for packaging and long term storage.
1. The sponges were placed into suitable containers and lyophilized again [using same lyophilizing cycle as provided in the chart above].
2. Crosslinked and lyophilized sponges were packaged as appropriate.

The details of the foregoing experiment which produced a placenta biosponge are set forth in the following Tables 1A and 1B, with the results and product characteristics reported in the "Results" column of Table 1B.

TABLE 1A

| Placenta Testing Matrix | | | |
|---|---|---|---|
| Metric | Specification | Method | Reference points |
| Mechanical properties | Option 1: Compression deflection force 2-4 kPa, 2-10 kPa (range) | CFD ASTM D3574-08 Peak compression (N) at 50% thickness using a 2 inch diameter compression platen | Current sponge values closer to 2-4 kPa |
| Mechanical properties (cont'd) | Option 2: Compressive strength comparable to current NPWT black foam or white foam | Compressive strength ASTM D1621 | |
| Fluid Flow through | At least 200 cc of SWF delivered at once, and delivered in increments of 25 ml is able to be evacuated at vacuum pressure ranges of 50, 125, 200 mmHg (KCI). Worst case: 50 mmHg To also monitor: % of fluid being drawn out 25 ml fluid drawn through within 30 seconds at 0, 24, 48, 72 hrs (NovoPore 510K compared to KCI Granufoam) - for info only for comparison against NPWT black foam or white foam | In vitro vac system | 1) "Low to moderate amounts of exudate" = 37.5 ml/day 2) KCI algorithm for SNAP single use system = ~26 ml/day (<180 ml/week) 3) Novopore 510k 4) KCI sponge + collagen dressing acceptance criteria 5) NPWT with instillation can be exposed to up to 100 cc of instillation fluid (saline or other) for 15 minute cycles |
| Durability - qualitative | 1) Does not crack when cut with scissors 2) Does not crack or disintegrate when wet and exposed to vacuum @ 200 mmHg | Simulated handling In vitro vac system | Normal handling during clinical use |
| Resorption | Stable for at least 5 days when exposed to SWF, "Stable" = | Enzymatic degradation in SWF - submersion in SWF @ 37 C. for 0, | 48-72 hrs change is standard for VAC therapies today, 5 dayseliminates a dressing |

TABLE 1A-continued

Placenta Testing Matrix

| Metric | Specification | Method | Reference points |
|---|---|---|---|
| | meets fluid flow through specs | 24, 48, 72, 96, 120 hrs hours and then exposure to vacuum system | change (Nichols) 7 days is the expiration of single use NPWT systems (SNAP therapy KCI) |
| Pore size | Approximately 160-270 um | SEM | Loh et al. 2013 cites, "Artel et al. 2011 showed that larger pore sizes of approximately 160 to 270 μm facilitated angiogenesis throughout scaffold" |
| Porosity | Percent porosity - no spec, just info only to provide comparison to NPWT black foam | Liquid Displacement | |
| Matrix Composition | Contains factors supporting granulation tissue formation, angiogenesis, and may contain anti-inflammatory factors | IHC | |

TABLE 1B

Placenta Testing Matrix

| Metric | References | Test article description | Results |
|---|---|---|---|
| Mechanical properties | (1) Lessing et al., NPWT with Controlled Saline Instillation, Wounds 2011: 23(1): pp. 309-319 | With final tissue yield from last process step as "100%" tissue mixture, used 50% mixture with lyo, with 1 hr crosslinking in 60 mM EDC/24 mM NHS in water with 4x 15 min water rinses and relyo after; | At 50% compression and saturated with liquid: 1) Saturated sample 17.048 kPa before, 9.633 kPa after 5 days 2) Immersed sample 13.721 kPa before, 5.415 kPa after 5 days Time 0 (Before 5-day incubation) 1) Saturated sample: 0.7108 g, center height 11.64 mm, edge heights 9.67, 9.92, 9.80 mm diameters 31.28, 31.19, 31.51 mm, peak force 13.14N 2) Immersed sample 0.7384 g, center height 11.59 mm, edge heights 11.02, 11.14, 11.21 mm diameters 31.01, 31.39, 31.69 mm, peak force 10.60N Post 5-day incubation 1) Saturated sample height 9.97 mm, diameter 33.91 mm, peak force 8.7N 2) Immersed sample height 12.22 mm, diameter 34.63 mm, peak force 5.1N |
| Mechanical properties (cont'd) | | — | N/A |
| Fluid Flow through | (2) FDA 510k K161432 (3) Acelity NPWT algorithm webinar/ brochure (4) FDA 510k K132936 (5) Westmoreland et al., An in vitro evaluation of a collagen/ORC/silver wound dressing under NPWT, SAWC Fall 2017 (6) Dettmers et al., Negative Pressure Wound Therapy With Instillation and Dwell Time Used to Treat Infected Orthopedic Implants: A 4-patient Case Series, 2016, 62(9): pp. 30-40 | — | Flow rates to pull 200 mL of simulated wound fluid (high pH buffer with high protein and protease content) all much higher than reported clinical exudate levels 1) T0 at 95 mmHg took 47 min (4.26 mL/min) Both saturated and immersed sample able to pull through 200 cc of SWF after 5 days in simulated CWF. 2) Saturated sample took 18 min 35 sec (10.76 mL/min) 3) Immersed sample took 76 min (2.63 mL/min) |
| Durability - qualitative | | — | spec equivalent to 50 mL/min, see data above 1) can be cut wet, when cut dry generates crumbs/flakes and can crack 2.1) T0 sample no crack after pulling 200 mmHg 2.2) Saturated sample no crack after pulling 200 mmHg 2.3) Immersed sample w/superficial crack after 200 mmHg but no loss of structural integrity, no tissue pulled into line |

TABLE 1B-continued

Placenta Testing Matrix

| Metric | References | Test article description | Results |
|---|---|---|---|
| Resorption | (9) Co-Inventor discussions 2017 | | Both saturated and immersed sample were stable, no tissue pulled into line |
| Pore size | (7) Loh QL et al., Three-dimensional scaffolds for tissue engineering applications: role of porosity and pore size. Tissue Eng Part B Rev. 2013; 19(6): 485-502. | | Crosslinked, dry, pore size via SEM imaging and ImageJ analysis: 158.59 um avg Feret diameter, range 37.82-1482.81 um, SD 19.266 um |
| Porosity | (8) Ho et al., A comparison of micro CT with other techniques used in the characerization of scaffolds, Biomaterials, 2006 v27, pp1362-1376 | | Range based on limited resolution of graduation markings: Granufoam: 88.9%-100% WHITEFOAM: 92.3%-100% Biosponge estimated 80%-85.7% |
| Matrix Composition | | | High levels of Col IV, ubiquitous Col III and HA. Low levels of GAGs. No PDGFb noted and traces of VEGF in 1 of 3 donors |

Example 2: Dermis Biosponge Prepared from Recovered Human Dermis Tissue

A dermis biosponge was prepared from human dermis tissue according to the general method shown in FIG. 6, with the specific parameters performed described below.

Initial Processing, Up Through Decellularization:

The deep layer of the reticular dermis (deep dermis) was first isolated from the full thickness dermis. The tissue was cut to smaller pieces by hand, then blended in a knife mill with a hypertonic solution to create a mixture. The mixture was agitated to decellularize the tissue components. The mixture was then blended again in the knife mill and then centrifuged. The pellet was resuspended in a surfactant solution and agitated to further decellularize the tissue components. The tissue was then subjected to a series of agitations in water to remove the surfactant solution.

1. The deep dermis was isolated from the full thickness dermis.
2. The deep dermis was frozen at −70° C. until further processing.
3. The deep dermis was thawed at room temperature.
4. The deep dermis was cut to smaller pieces using scissors or a rolling blade cutter.
5. The cut tissue was added to the container of the knife mill (GM200) with 1M NaCl at a ratio of 1:4 tissue to solution by weight.
6. The tissue mixture was blended for 10 seconds at 7000 rpm, then 20 seconds for 10000 rpm, then 20 seconds for 10000 rpm.
7. The tissue mixture was transferred to a 2 L flask and agitated on an orbital shaker at 150 rpm for 12-24 hours.
8. The tissue mixture was poured directly into the container of the knife mill.
9. The tissue mixture was blended again using the previously mentioned parameters.
10. The tissue mixture was centrifuged.
11. The pelleted tissue was resuspended in 0.10% Triton X solution.
12. The tissue mixture was transferred to a 2 L flask and agitated on an orbital shaker at 150 rpm for 24-28 hours.
13. The tissue was separated from the 0.10% Triton X solution using a centrifuge or sieve.
14. The tissue was added to water for rinsing and agitated on an orbital shaker at 150 rpm for 5 minutes.
15. The tissue was separated from the water using a centrifuge or sieve.
16. This was repeated for a total of eight water rinses.
17. The tissue was frozen at −70° C. (or −20° C. or −80° C.) until further processing.

Disinfection (i.e., Reducing Microbial Load):

The decellularized tissue is thawed and agitated with a peracetic acid-based disinfection solution to disinfect the tissue. The tissue mixture is then blended in the knife mill, followed by four neutralization rinses in 1×DPBS solution, with centrifugation after each. The remaining tissue is combined with water in a variety of potential ratios to create a tissue mixture, which is then transferred to a mold prior to lyophilization.

11. The tissue was thawed at room temperature.
12. The tissue was added to a 2 L flask with 1 L of peracetic acid based disinfection solution.
13. The tissue mixture was agitated on an orbital shaker at 150 rpm for 2-4 hours.
14. The tissue mixture was added directly to the container of the knife mill and blended using the previously mentioned parameters.
15. The tissue mixture was centrifuged to remove the disinfection solution and to produce a pellet.
16. The pellet was resuspended in 1×DPBS in a 2 L flask and agitated on an orbital shaker at 150 rpm for 5-20 min.
17. The tissue mixture was centrifuged to remove the 1×DPBS.
18. This was repeated for a total of four 1×DPBS neutralization rinses.
19. The tissue was mixed by hand with water to a ratio of 25:75 tissue to water by weight.
20. The tissue mixture was transferred to a mold to create the desired shape.

Drying/Lyophilization:

The tissue mixture was dried by lyophilizing: the tissue in the mold was placed into a lyophilizer and the following lyophilization cycle was run to obtain a dried tissue form (sponge)

1. The lyophilization parameters used were:
    a. Ramp to −40° C. at 1° C./min
    b. Primary drying at −5° C. or less for more than 48 hours
    c. Secondary drying at 25° C. for at least 8 hours Crosslinking and Final Drying/Lyophilization:

Cross-linking and final lyophilization was performed as was described in the cross-linking section of Example 1.

The details of the foregoing experiment which produced a dermal biosponge are set forth in the following Tables 2A and 2B, with the results and product characteristics reported in the "Results" column of Table 2B.

TABLE 2A

Dermis Testing Matrix

| Metric | Specification | Method | Reference points |
|---|---|---|---|
| Mechanical properties | Option 1: Compression deflection force 2-4 kPa, 2-10 kPa (range) | CFD ASTM D3574-08 Peak compression (N) at 50% thickness using a 2 inch diameter compression platen | Current sponge values closer to 2-4 kPa |
| Mechanical properties (cont'd) | Option 2: Compressive strength comparable to current NPWT black foam or white foam | Compressive strength ASTM D1621 | |
| Fluid Flow through | At least 200cc of SWF delivered at once, and delivered in increments of 25 ml is able to be evacuated at vacuum pressure ranges of 50, 125, 200 mmHg (KCI). Worst case: 50 mmHg To also monitor: % of fluid being drawn out | In vitro vac system | 1) "Low to moderate amounts of exudate" = 37.5 ml/day 2) KCI algorithm for SNAP single use system = ~26 ml/day (<180 ml/week) 3) Novopore 510k 4) KCI sponge + collagen dressing acceptance criteria 5) NPWT with instillation can be exposed to up to 100 cc of instillation fluid (saline or other) for 15 minute cycles |
| Fluid Flow through (continued) | 25 ml fluid drawn through within 30 seconds at 0, 24, 48, 72 hrs (NovoPore 510K compared to KCI Granufoam) - for info only for comparison against NPWT black foam or white foam | | |
| Durability - qualitative | 1) Does not crack when cut with scissors 2) Does not crack or disintegrate when wet and exposed to vacuum @ 200 mmHg | Simulated handling In vitro vac system | Normal handling during clinical use |
| Resorption | Stable for at least 5 days when exposed to SWF, "Stable" = meets fluid flow through specs | Enzymatic degradation in SWF - submersion in SWF @ 37 C. for 0, 24, 48, 72, 96, 120 hrs ours and then exposure to vacuum system | 48-72 hrs change is standard for VAC therapies today, 5 days eliminates a dressing change (Nichols) 7 days is the expiration of single use NPWT systems (SNAP therapy KCI) |
| Pore size | At least 100 um, mean target closer to 300-400 um | SEM | "Vascularization of constructs necessitates pores greater than 300 μm" |

TABLE 2B

Dermis Testing Matrix

| Metric | References | Test article description | Results |
|---|---|---|---|
| Mechanical properties | (1) Lessing et al., NPWT with Controlled Saline Instillation, Wounds 2011: 23(1): pp. 309-319 | With final tissue yield from last process step as "100%" tissue mixture. Time 0 measurement: 1.5 cm thick 30:70 tissue:water wet weight 1 hour xlink with EDC-NHS | Time 0: 4.24 kPa Time 5 days: 2.66 kPa |

TABLE 2B-continued

Dermis Testing Matrix

| Metric | References | Test article description | Results |
|---|---|---|---|
| Mechanical properties (cont'd) | | — | N/A |
| Fluid Flow through | (2) FDA 510k K161432<br>(3) Acelity NPWT algorithm webinar/brochure<br>(4) FDA 510k K132936<br>(5) Westmoreland et al., An in vitro evaluation of a collagen/ORC/silver wound dressing under NPWT, SAWC Fall 2017<br>(6) Dettmers et al., Negative Pressure Wound Therapy With Instillation and Dwell Time Used to Treat Infected Orthopedic Implants: A 4-patient Case Series, 2016, 62(9): pp. 30-40 | | Time 0: At 100 mmHg, 175 ml (200 cc but 25 ml stuck in system) took 17 min 14 secs (10.16 ml/min)<br>Time 5 days: At 100 mmHg, 57 ml (80 cc but 23 ml stuck in system) took 5 mins (11.4 ml/min) |
| Durability - qualitative | | | see above<br>1) can be cut wet, can be cut dry with scalpel recommended 2) no cracking when pulled at 200 mmHg<br>2.1) Time 5 days in SWF: no cracking when pulled at 200 mmHg |
| Resorption | (9) Co-Inventor discussions 2017 | | Time 0: Stable, no tissue through line<br>Time 5 days: Stable, no tissue through line |
| Pore size | (7) Loh QL et al., Three-dimensional scaffolds for tissue engineering applications: role of porosity and pore size. Tissue Eng Part B Rev. 2013; 19(6): 485-502. | | Crosslinked, dry pore size by SEM imaging and ImageJ analysis: 149.25 +/− 8.49 avg Ferret diameter, min 85.28 |

Example 3: Dermal Biosponge Characterization

Figure 6:
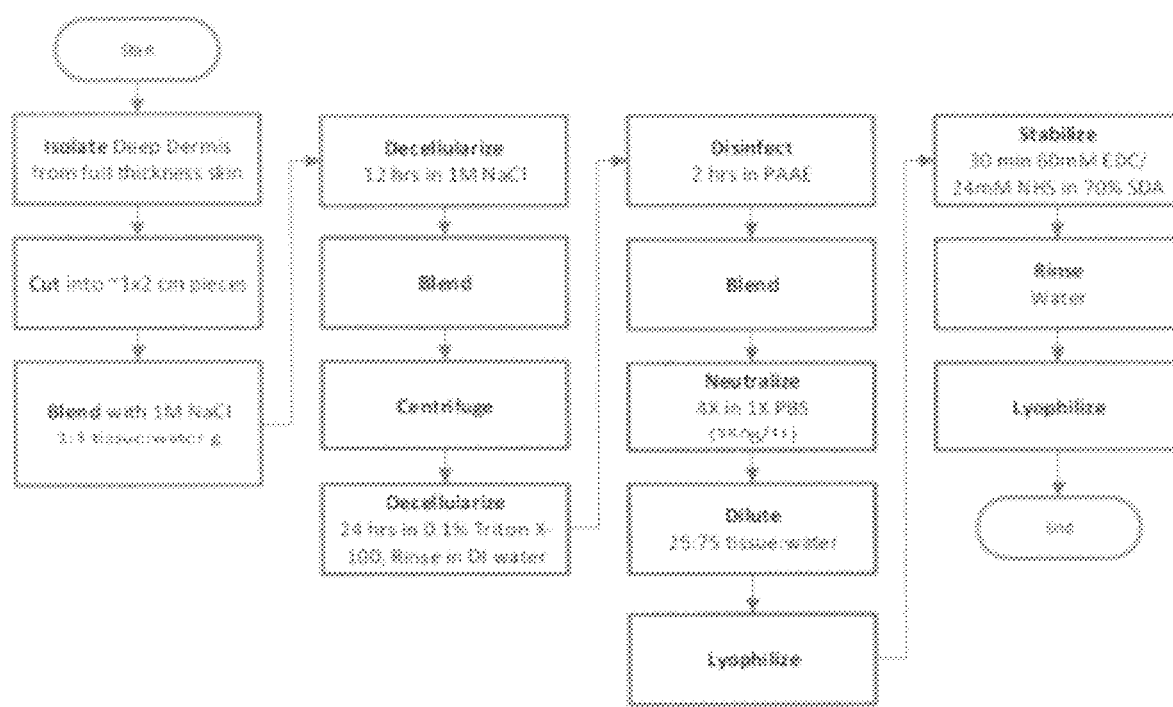
FIG. 6 is a flowchart showing the basic steps of an exemplary method for producing tissue derived porous matrices comprising dermis tissue (a dermis biosponge) in accordance with the present invention.

Another dermis biosponge was prepared from human dermis tissue according to the general method shown in FIG. 6. The details of this experiment which produced another dermal biosponge are set forth in the following Tables 3A and 3B, with the results and product characteristics reported in the "Results" column of Table 3B.

In particular, it is noted that for this Example 3, the tissue derived porous matrices were produced from dermis tissue using:

a ratio of tissue to NaCl solution of 1:8 (by weight), rather than 1:4 as in Example 2;
a 30:70 tissue to water dilution, rather than 25:75 as in Example 2; and
2 hour stabilization (crosslinking) in 6 mM EDC/2.4 nM NHS crosslinking solution, rather than 30 minutes in 60 mM EDC/24 mM NHS as in Example 2.

TABLE 3A

Dermis Testing Matrix

| Metric | Specification | Method |
|---|---|---|
| Unconfined Compression | Comparable to current NPWT black foam or white foam | Unconfined Compression Testing |
| Stress-Relaxation | Comparable to current NPWT black foam or white foam | Compressive Stress-Relaxation Testing |
| Rheology | Comparable to current NPWT black foam or white foam | Rheological Testing |
| Fluid Flow through | Comparable to current NPWT black foam or white foam | Fluid Flow Testing (using syringe pump) |
| Resorption | Stable after exposure to BSA | Degradation Testing - Storage for 7 or 14 days in BSA at 37 C. then compressive and rheological testing as above |
| Hydration | Comparable to current NPWT black foam or hite foam | Hydration Testing (Percent mass change after storage in PBS) |

TABLE 3B

Dermis Testing Matrix

| Metric | Test article description | Results |
|---|---|---|
| Unconfined Compression | 1.5 × 1.5 × 2 cm Rehydrated in PBS | Compressive Moduli:<br>Biosponge: 32.56 +/− 5.87 kPA<br>GranuFoam: 8.80 kPA<br>Resilience:<br>Biosponge: 2.44 +/− 0.33 J/m3<br>GranuFoam: 0.95 J/m3 |
| Stress-Relaxation | 1.5 × 1.5 × 2 cm Rehydrated in PBS | Time constant values ($\tau$):<br>Biosponge: $\tau 1$ = 1.07 +/− 0.34, $\tau 2$ = 1.07 +/− 0.41 |
| Rheology | 1.5 × 1.5 × 2 cm Rehydrated in PBS | Shear Modulus @ 1rad/s (kPa):<br>Biosponge: 3.21 +/− 0.94 |

TABLE 3B-continued

Dermis Testing Matrix

| Metric | Test article description | Results |
|---|---|---|
| | | GranuFoam: 3.96 |
| | | Shear Modulus @ 10 rad/s (kPA): |
| | | Biosponge: 3.25 +/− 0.88 |
| | | GranuFoam: 4.69 |
| Fluid Flow through | 28 mm diameter samples | Flow Resistance (psi min/L): Biosponge: 6.47 +/− 0.97 |
| | | GranuFoam: 6.68 |
| Resorption | 1.5 × 1.5 × 2 cm rehydrated in BSA | See plots to right |
| Hydration | 1.5 × 1.5 × 2 cm | Average % Mass Change: Biosponge: 2157 +/− 136 GranuFoam: 2413 +/−199 |

Example 4: Dermis Biosponge Prepared from Recovered Human Dermis Tissue

Figure 7:
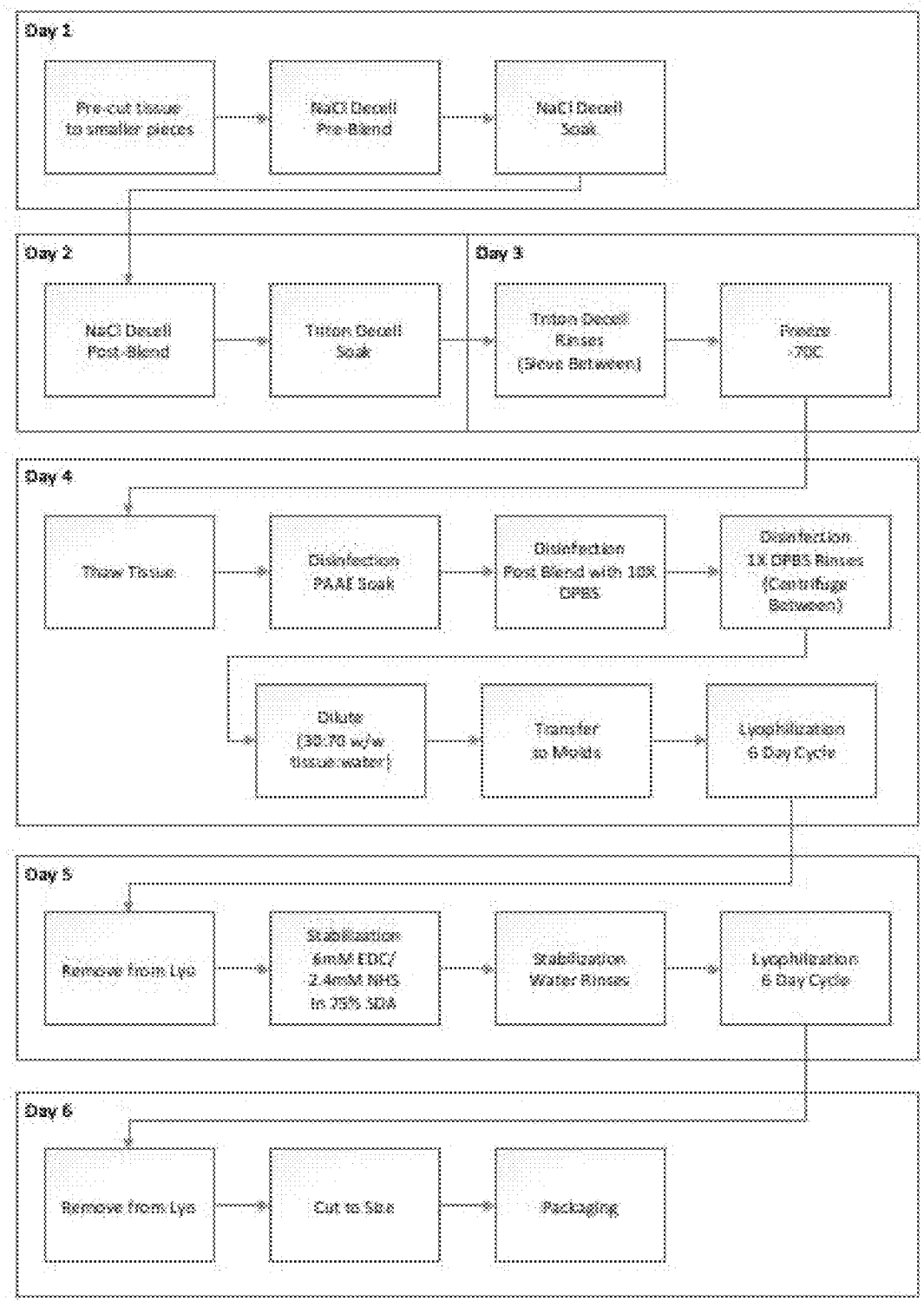
FIG. 7 is a flowchart showing the steps of an exemplary method for producing tissue derived porous matrices comprising dermis tissue (a dermis biosponge) in accordance with the present invention.

Still another dermis biosponge was prepared from human dermis tissue according to the more detailed method shown in FIG. 7, with the specific parameters performed described below.

Cutting and Decellularization

The deep layer of the reticular dermis (deep dermis) is first isolated from the full thickness dermis. The deep dermis may then optionally be frozen at −70° C. until further processing.

The deep dermis is cut to smaller pieces, approximately 2×2 cm in size or smaller, using a rolling blade cutter. The cut tissue is added to 1M NaCL solution into the container of a knife mill (GM300, Retsch). The tissue and solution are blended first at 2500 rpm for 20 s and then subsequently at 4000 rpm for 2 minutes with 20 s intervals. The blended tissue mixture is then transferred to flasks and soaked in the 1M NaCl for 12-48 hours on a shaker at 150 rpm. Following completion of the soak the tissue mixture is transferred to the knife mill and blended first at 2500 rpm for 20 s and then subsequently at 4000 rpm for 2 minutes with 20 s intervals. After blending the tissue mixture is centrifuged at 4600 rpm for 5 minutes and the supernatant is poured off. The pelleted tissue is added to a 0.1% Triton solution and soaked for 24-48 hrs at 150 rpm. Following the soak, the tissue is separated from the solution using a 90-110 μm sieve. The tissue then goes through a sequence of eight 5 minute water rinses on a shaker at 150 rpm. The tissue is separated from the water after each rinse using a 90-110 μm sieve. Upon completion of the rinses the tissue is frozen at −70° C. until further process.

Disinfection and Start of Lyophilization

The frozen tissue is thawed and excess water is separated from the tissue using a 90-110 μm sieve. The tissue is added to a solution containing peracetic acid, ethanol, and propylene glycol and soaked for 2-4 hours on a shaker at 150 rpm. Following completion of the soak the tissue mixture is transferred to the knife mill along with 10×DPBS to neutralize the acid. The tissue mixture is blended at 4000 rpm for 2 minutes with 20 s intervals. Following blending the tissue mixture is centrifuged at 4600 rpm for 5 minutes and the supernatant is poured off. The tissue then goes through three 5 minute rinses in 1×DPBS on a shaker at 150 rpm, with a centrifuge step at 4600 rpm for 5 minutes after each rinse to separate the tissue from the rinsate. Upon completion of the rinses the tissue is diluted with water to create a tissue slurry (ie. 30:70 tissue to water, w:w). The tissue slurry is transferred to molds and placed into a lyophilizer. An appropriate lyophilization cycle is run to obtain a dried tissue form. The technique for performing lyophilization is not particularly limited and may be any technique known now or in the future to persons of ordinary skill in the relevant art.

Stabilization and Start of Second Lyophilization

Stabilization is performed as described in the cross-linking section of Example 1. Upon completion of cross-linking the tissue is placed back in its molds with water and placed into a lyophilizer. The same recipe as previous is run to obtain a dried final tissue form. The dry tissue is stored in packaging suitable for long term storage.

It will be understood that the embodiments of the present invention described hereinabove are merely exemplary and that a person skilled in the art may make variations and modifications without departing from the spirit and scope of the invention. All such variations and modifications are intended to be included within the scope of the present invention.

We claim:

1. A method for producing a tissue derived porous matrix which is resorbable and has a plurality of interconnected pores which allow fluid flow through the matrix, the method comprising the steps of: obtaining a sample of non-neonatal mammalian tissue selected from dermis, adipose, fascia, and combinations thereof and having a native porosity; reducing the size of the mammalian tissue one or more times; forming or modifying pores; drying the mammalian tissue to produce a dried mammalian tissue having a porous structure; stabilizing the dried mammalian tissue by at least partially crosslinking by contacting the dried mammalian tissue with a crosslinking solution for a period of time, and then removing excess crosslinking solution by performing one or more rinses and at least partially compressing the crosslinked mammalian tissue to separate additional excess crosslinking solution from the crosslinked mammalian tissue, which produces a crosslinked mammalian tissue having a partially collapsed porous structure; and restoring at least a portion of the partially collapsed porous structure by contacting the crosslinked mammalian tissue with an aqueous solvent for a period of time, and then drying the crosslinked mammalian tissue a second time by lyophilizing, which produces a dried, crosslinked mammalian tissue having a porous structure with increased thickness and increased porosity compared to the crosslinked mammalian tissue produced by the stabilizing step, wherein the increased porosity is from about 50% to about 99%.

2. The method of claim 1, further comprising the step of formulating by mixing, attaching, or otherwise combining the tissue derived porous matrix with one or more additional biocompatible materials or other synthetic or naturally-derived matrices.

3. The method of claim 1, wherein the step of reducing the size of the mammalian tissue one or more times is performed by cutting, blending, milling, or a combination thereof.

4. The method of claim 1, further comprising one or more of the following steps:
one or both of delipidating and demineralizing the mammalian tissue;
decellularizing the mammalian tissue;
disinfecting the mammalian tissue;
combining a solvent with the mammalian tissue;
after performing the step of reducing the size of the mammalian tissue at least one time,
placing the mammalian tissue in a container or mold; and
disinfecting the crosslinked tissue.

5. The method of claim 4, wherein the step of disinfecting the tissue comprises sterilizing the tissue, either before or after the drying step, or both.

6. The method of claim 4, wherein the step of combining a solvent with the tissue is performed prior to the drying step and the solvent is water, wherein a tissue and water mixture is formed, and wherein the steps of forming or modifying pores and drying the tissue are performed concurrently by lyophilizing the tissue and water mixture.

7. A tissue derived porous matrix produced by the method of claim 1 and comprising a processed tissue which is a three-dimensional scaffold derived from a sample of non-neonatal mammalian tissue selected from dermis, adipose, fascia, and combinations thereof and having a native porosity, wherein the matrix is resorbable, has a plurality of interconnected pores which allow fluid flow through the matrix, and is at least partially cross-linked which stabilizes the matrix and provides a controlled resorption rate after implantation, wherein the tissue derived porous matrix has increased thickness and increased porosity compared to an at least partially crosslinked mammalian tissue which has not been subjected to contacting with an aqueous solvent and drying after crosslinking has been performed, wherein the increased porosity is from about 50% to about 99%, and wherein the tissue derived porous matrix lacks a manifold layer, or lacks a release material layer, or lacks both.

8. The tissue derived porous matrix of claim 7, wherein when the matrix is implanted, in contact or proximity, with a wound site of a subject, the matrix at least partially degrades, partially remodels with native tissue at the wound site, or both, wherein no portion of the matrix need be removed from the wound site after being positioned with the wound.

9. The tissue derived porous matrix of claim 8, wherein the matrix has a desired shape and has been lyophilized in a container or mold having the desired shape.

10. The tissue derived porous matrix of claim 7, wherein when implanted in proximity or contact with a wound site of a subject, fluid flow from the wound site and through the matrix occurs, with or without application of reduced pressure, during healing at the wound site.

11. The tissue derived porous matrix of claim 7, further comprising one or more endogenous beneficial substances.

12. A biocompatible composition comprising the tissue derived porous matrix of claim 7 and one or more additional biocompatible materials.

13. A wound dressing for treating a wound site comprising:
a porous component comprising the tissue derived porous matrix of claim 7; and
a semipermeable barrier component sized and shaped to cover the porous component and
a wound site to be treated with the wound dressing.

14. A method for treating a wound comprising implanting the tissue derived porous matrix of claim 7, in contact or proximity, with a wound site of a subject, wherein the matrix comprises a tissue having a plurality of interconnected pores which allow fluid flow through the matrix and the matrix is resorbable.

* * * * *